United States Patent [19]

Hung et al.

[11] Patent Number: 5,045,315

[45] Date of Patent: Sep. 3, 1991

[54] PROCESS FOR TREATING THROMBOSIS BY ADMINISTERING POLY-KRINGLE PLASMINOGEN ACTIVATOR

[75] Inventors: Paul P. Hung, Bryn Mawr; Narender K. Kalyan, King of Prussia; Shaw-guang L. Lee, Villanova, all of Pa.

[73] Assignee: American Home Products Corporation, New York, N.Y.

[21] Appl. No.: 601,542

[22] Filed: Oct. 23, 1990

Related U.S. Application Data

[60] Division of Ser. No. 436,528, Nov. 14, 1989, Pat. No. 4,997,766, which is a division of Ser. No. 884,835, Jul. 11, 1986, Pat. No. 4,916,071, which is a continuation-in-part of Ser. No. 766,163, Aug. 14, 1985, abandoned.

[51] Int. Cl.$^5$ .................. A61K 37/547; A61K 37/54; C12N 9/48; C12N 9/64
[52] U.S. Cl. .............. 424/94.64; 424/94.63; 424/94.2; 435/212; 435/215; 435/226; 435/214
[58] Field of Search .................... 424/94.63, 94.64; 435/212, 214, 215, 226

[56] References Cited

U.S. PATENT DOCUMENTS 4,752,581 6/1988 Robinson et al. .................. 435/212
4,766,075 8/1988 Goeddel et al. .................. 435/212

OTHER PUBLICATIONS

Nelles, L. et al., *J. Biol. Chem.*, vol. 262, pp. 10855–10862, 1987.
Gheysen, D. et al., *J. Biol. Chem.*, vol. 262, pp. 11779–11784, 1987.
Pierardi, L. et al., *J. Biol. Chem.*, vol. 262, pp. 11771–11778, 1987.

*Primary Examiner*—Richard A. Schwartz
*Assistant Examiner*—Marianne Porta
*Attorney, Agent, or Firm*—Richard K. Jackson

[57] ABSTRACT

Hybrid, third generation, plasminogen activators containing plural, heterologous polypeptide kringles prepared by recombinant DNA techniques as well as the genes coding for the activators, Vectors containing those genes and a method for using the plasminogen activators as thrombolytic agents, are disclosed.

5 Claims, 37 Drawing Sheets

TRIS-KRINGLE PA, OF FIG. (1a)

```
                                                          32
GGATCCTCGAC ATG AGA GCC CTG CTG GCG CGC
            Met Arg Ala Leu Leu Ala Arg

62
CTG CTT CTC TGC GTC CTG GTC GTG AGC GAC
Leu Leu Leu Cys Val Leu Val Val Ser Asp

92
TCC AAA GGC AGC AAT GAA CTT CAT CAA GTT
Ser Lys Gly Ser Asn Glu Leu His Gln Val

122
CCA TCG AAC TGT GAC TGT CTA AAT GGA GGA
Pro Ser Asn Cys Asp Cys Leu Asn Gly Gly

152
ACA TGT GTG TCC AAC AAG TAC TTC TCC AAC
Thr Cys Val Ser Asn Lys Tyr Phe Ser Asn

182
ATT CAC TGG TGC AAC TGC CCA AAG AAA TTC
Ile His Trp Cys Asn Cys Pro Lys Lys Phe

212
GGA GGG CAG CAC TGT GAA ATA GAT AAG TCA
Gly Gly Gln His Cys Glu Ile Asp Lys Ser

242
AAA ACC TGC TAT GAG GGG AAT GGT CAC TTT
Lys Thr Cys Tyr Glu Gly Asn Gly His Phe
```

Figure 9

TRIS-KRINGLE PA, OF FIG. (1a)

|     |     |     |     |     |     |     |     |     | 272 |
| --- | --- | --- | --- | --- | --- | --- | --- | --- | --- |
| TAC | CGA | GGA | AAG | GCC | AGC | ACT | GAC | ACC | ATG |
| Tyr | Arg | Gly | Lys | Ala | Ser | Thr | Asp | Thr | Met |

|     |     |     |     |     |     |     |     |     | 302 |
| --- | --- | --- | --- | --- | --- | --- | --- | --- | --- |
| GGC | CGG | CCC | TGC | CTG | CCC | TGG | AAC | TCT | GCC |
| Gly | Arg | Pro | Cys | Leu | Pro | Trp | Asn | Ser | Ala |

|     |     |     |     |     |     |     |     |     | 332 |
| --- | --- | --- | --- | --- | --- | --- | --- | --- | --- |
| ACT | GTC | CTT | CAG | CAA | ACG | TAC | CAT | GCC | CAC |
| Thr | Val | Leu | Gln | Gln | Thr | Tyr | His | Ala | His |

|     |     |     |     |     |     |     |     |     | 362 |
| --- | --- | --- | --- | --- | --- | --- | --- | --- | --- |
| ACA | TCT | GAT | GCT | CTT | CAG | CTG | GGC | CTG | GGG |
| Arg | Ser | Asp | Ala | Leu | Gln | Leu | Gly | Leu | Gly |

|     |     |     |     |     |     |     |     |     | 392 |
| --- | --- | --- | --- | --- | --- | --- | --- | --- | --- |
| AAA | CAT | AAT | TAC | TGC | AGG | AAC | CCA | GAC | AAC |
| Lys | His | Asn | Tyr | Cys | Arg | Asn | Pro | Asp | Asn |

|     |     |     |     |     |     |     |     |     | 422 |
| --- | --- | --- | --- | --- | --- | --- | --- | --- | --- |
| CGG | AGG | CGA | CCC | TGG | TGC | TAT | GTG | CAG | GTG |
| Arg | Arg | Arg | Pro | Trp | Cys | Tyr | Val | Gln | Val |

|     |     |     |     |     |     |     |     |     | 452 |
| --- | --- | --- | --- | --- | --- | --- | --- | --- | --- |
| GGC | CTA | AAG | CCG | CTT | GTC | CAA | GAG | TGC | ATG |
| Gly | Leu | Lys | Pro | Leu | Val | Gln | Glu | Cys | Met |

|     |     |     |     |     |     |     |     |     | 482 |
| --- | --- | --- | --- | --- | --- | --- | --- | --- | --- |
| GTG | CAT | GAC | TGC | AGC | GAG | GGC | AAC | TCC | GAC |
| Val | His | Asp | Cys | Ser | Glu | Gly | Asn | Ser | Asp |

Figure 9a

TRIS-KRINGLE PA, OF FIG. (1a)

```
                                                            512
TGC TAC GAG GAC CAG GGC ATC AGC TAC AGG
Cys Tyr Glu Asp Gln Gly Ile Ser Tyr Arg

542
GGC ACG TGG AGC ACA GCG GAG AGT GGC GCC
Gly Thr Trp Ser Thr Ala Glu Ser Gly Ala

572
GAG TGC ACC AAC TGG AAC AGC AGC GCG TTG
Glu Cys Thr Asn Trp Asn Ser Ser Ala Leu

602
GCC CAG AAG CCC TAC AGC GGG CGG AGG CCA
Ala Gln Lys Pro Tyr Ser Gly Arg Arg Pro

632
GAC GCC ATC AGG CTG GGC CTG GGG AAC CAC
Asp Ala Ile Arg Leu Gly Leu Gly Asn His

662
AAC TAC TGC AGA AAC CCA GAT CGA GAC TCA
Asn Tyr Cys Arg Asn Pro Asp Arg Asp Ser

692
AAG CCC TGG TGC TAC GTC TTT AAG GCG GGG
Lys Pro Trp Cys Tyr Val Phe Lys Ala Gly

722
AAG TAC AGC TCA GAG TTC TGC AGC ACC CCT
Lys Tyr Ser Ser Glu Phe Cys Ser Thr Pro
```

Figure 9b

TRIS-KRINGLE PA, OF FIG. (1a)

| | | | | | | | | | 752 |
|---|---|---|---|---|---|---|---|---|---|
| GCC | TGC | TCT | GAG | GGA | AAC | AGT | GAC | TGC | TAC |
| Ala | Cys | Ser | Glu | Gly | Asn | Ser | Asp | Cys | Tyr |

| | | | | | | | | | 782 |
|---|---|---|---|---|---|---|---|---|---|
| TTT | GGG | AAT | GGG | TCA | GCC | TAC | CGT | GGC | ACG |
| Phe | Gly | Asn | Gly | Ser | Ala | Tyr | Arg | Gly | Thr |

| | | | | | | | | | 812 |
|---|---|---|---|---|---|---|---|---|---|
| CAC | AGC | CTC | ACC | GAG | TCG | GGT | GCC | TCC | TGC |
| His | Ser | Leu | Thr | Glu | Ser | Gly | Ala | Ser | Cys |

| | | | | | | | | | 842 |
|---|---|---|---|---|---|---|---|---|---|
| CTC | CCG | TGG | AAT | TCC | ATG | ATC | CTG | ATA | GGC |
| Leu | Pro | Trp | Asn | Ser | Met | Ile | Leu | Ile | Gly |

| | | | | | | | | | 872 |
|---|---|---|---|---|---|---|---|---|---|
| AAG | GTT | TAC | ACA | GCA | CAG | AAC | CCC | AGT | GCC |
| Lys | Val | Tyr | Thr | Ala | Gln | Asn | Pro | Ser | Ala |

| | | | | | | | | | 902 |
|---|---|---|---|---|---|---|---|---|---|
| CAG | GCA | CTG | GGC | CTG | GGC | AAA | CAT | AAT | TAC |
| Gln | Ala | Leu | Gly | Leu | Gly | Lys | His | Asn | Tyr |

| | | | | | | | | | 932 |
|---|---|---|---|---|---|---|---|---|---|
| TGC | CGG | AAT | CCT | GAT | GGG | GAT | GCC | AAG | CCC |
| Cys | Arg | Asn | Pro | Asp | Gly | Asp | Ala | Lys | Pro |

| | | | | | | | | | 962 |
|---|---|---|---|---|---|---|---|---|---|
| TGG | TGC | CAC | GTG | CTG | AAG | AAC | CGC | AGG | CTG |
| Trp | Cys | His | Val | Leu | Lys | Asn | Arg | Arg | Leu |

Figure 9c

TRIS-KRINGLE PA, OF FIG. (1a)

|     |     |     |     |     |     |     |     |     | 992 |
|-----|-----|-----|-----|-----|-----|-----|-----|-----|-----|
| ACG | TGG | GAG | TAC | TGT | GAT | GTG | CCC | TCC | TGC |
| Thr | Trp | Glu | Tyr | Cys | Asp | Val | Pro | Ser | Cys |

|     |     |     |     |     |     |     |     |     | 1022 |
|-----|-----|-----|-----|-----|-----|-----|-----|-----|------|
| TCC | ACC | TGC | GGC | CTG | AGA | CAG | TAC | AGC | CAG  |
| Ser | Thr | Cys | Gly | Leu | Arg | Gln | Tyr | Ser | Gln  |

|     |     |     |     |     |     |     |     |     | 1052 |
|-----|-----|-----|-----|-----|-----|-----|-----|-----|------|
| CCT | CAG | TTT | CGC | ATC | AAA | GGA | GGG | CTC | TTC  |
| Pro | Gln | Phe | Arg | Ile | Lys | Gly | Gly | Leu | Phe  |

|     |     |     |     |     |     |     |     |     | 1082 |
|-----|-----|-----|-----|-----|-----|-----|-----|-----|------|
| GCC | GAC | ATC | GCC | TCC | CAC | CCC | TGG | CAG | GCT  |
| Ala | Asp | Ile | Ala | Ser | His | Pro | Trp | Gln | Ala  |

|     |     |     |     |     |     |     |     |     | 1112 |
|-----|-----|-----|-----|-----|-----|-----|-----|-----|------|
| GCC | ATC | TTT | GCC | AAG | CAC | AGG | AGG | TCG | CCC  |
| Ala | Ile | Phe | Ala | Lys | His | Arg | Arg | Ser | Pro  |

|     |     |     |     |     |     |     |     |     | 1142 |
|-----|-----|-----|-----|-----|-----|-----|-----|-----|------|
| GGA | GAG | CGG | TTC | CTG | TGC | GGG | GGC | ATA | CTC  |
| Gly | Glu | Arg | Phe | Leu | Cys | Gly | Gly | Ile | Leu  |

|     |     |     |     |     |     |     |     |     | 1172 |
|-----|-----|-----|-----|-----|-----|-----|-----|-----|------|
| ATC | AGC | TCC | TGC | TGG | ATT | CTC | TCT | GCC | GCC  |
| Ile | Ser | Ser | Cys | Trp | Ile | Leu | Ser | Ala | Ala  |

|     |     |     |     |     |     |     |     |     | 1202 |
|-----|-----|-----|-----|-----|-----|-----|-----|-----|------|
| CAC | TGC | TTC | CAG | GAG | AGG | TTT | CCG | CCC | CAC  |
| His | Cys | Phe | Gln | Glu | Arg | Phe | Pro | Pro | His  |

Figure 9d

TRIS-KRINGLE PA, OF FIG. (1a)

| | | | | | | | | | 1232 |
|---|---|---|---|---|---|---|---|---|---|
| CAC | CTG | ACG | GTG | ATC | TTG | GGC | AGA | ACA | TAC |
| His | Leu | Thr | Val | Ile | Leu | Gly | Arg | Thr | Tyr |

| | | | | | | | | | 1262 |
|---|---|---|---|---|---|---|---|---|---|
| CGG | GTG | GTC | CCT | GGC | GAG | GAG | GAG | CAG | AAA |
| Arg | Val | Val | Pro | Gly | Glu | Glu | Glu | Gln | Lys |

| | | | | | | | | | 1292 |
|---|---|---|---|---|---|---|---|---|---|
| TTT | GAA | GTC | GAA | AAA | TAC | ATT | GTC | CAT | AAG |
| Phe | Glu | Val | Glu | Lys | Tyr | Ile | Val | His | Lys |

| | | | | | | | | | 1322 |
|---|---|---|---|---|---|---|---|---|---|
| GAA | TTC | GAT | GAT | GAC | ACT | TAC | GAC | AAT | GAC |
| Glu | Phe | Asp | Asp | Asp | Thr | Tyr | Asp | Asn | Asp |

| | | | | | | | | | 1352 |
|---|---|---|---|---|---|---|---|---|---|
| ATT | GCG | CTG | CTG | CAG | CTG | AAA | TCG | GAT | TCG |
| Ile | Ala | Leu | Leu | Gln | Leu | Lys | Ser | Asp | Ser |

| | | | | | | | | | 1382 |
|---|---|---|---|---|---|---|---|---|---|
| TCC | CGC | TGT | GCC | CAG | GAG | AGC | AGC | GTG | GTC |
| Ser | Arg | Cys | Ala | Gln | Glu | Ser | Ser | Val | Val |

| | | | | | | | | | 1412 |
|---|---|---|---|---|---|---|---|---|---|
| CGC | ACT | GTG | TGC | CTT | CCC | CCG | GCG | GAC | CTG |
| Arg | Thr | Val | Cys | Leu | Pro | Pro | Ala | Asp | Leu |

| | | | | | | | | | 1442 |
|---|---|---|---|---|---|---|---|---|---|
| CAG | CTG | CCG | GAC | TGG | ACG | GAG | TGT | GAG | CTC |
| Gln | Leu | Pro | Asp | Trp | Thr | Glu | Cys | Glu | Leu |

Figure 9e

TRIS-KRINGLE PA, OF FIG. (1a)

|  |  |  |  |  |  |  |  |  | 1472 |
|---|---|---|---|---|---|---|---|---|---|
| TCC | GGC | TAC | GGC | AAG | CAT | GAG | GCC | TTG | TCT |
| Ser | Gly | Tyr | Gly | Lys | His | Glu | Ala | Leu | Ser |

|  |  |  |  |  |  |  |  |  | 1502 |
|---|---|---|---|---|---|---|---|---|---|
| CCT | TTC | TAT | TCG | GAG | CGG | CTG | AAG | GAG | GCT |
| Pro | Phe | Tyr | Ser | Glu | Arg | Leu | Lys | Glu | Ala |

|  |  |  |  |  |  |  |  |  | 1532 |
|---|---|---|---|---|---|---|---|---|---|
| CAT | GTC | AGA | CTG | TAC | CCA | TCC | AGC | CGC | TGC |
| His | Val | Arg | Leu | Tyr | Pro | Ser | Ser | Arg | Cys |

|  |  |  |  |  |  |  |  |  | 1562 |
|---|---|---|---|---|---|---|---|---|---|
| ACA | TCA | CAA | CAT | TTA | CTT | AAC | AGA | ACA | GTC |
| Thr | Ser | Gln | His | Leu | Leu | Asn | Arg | Thr | Val |

|  |  |  |  |  |  |  |  |  | 1592 |
|---|---|---|---|---|---|---|---|---|---|
| ACC | GAC | AAC | ATG | CTG | TGT | GCT | GGA | GAC | ACT |
| Thr | Asp | Asn | Met | Leu | Cys | Ala | Gly | Asp | Thr |

|  |  |  |  |  |  |  |  |  | 1622 |
|---|---|---|---|---|---|---|---|---|---|
| CGG | AGC | GGC | GGG | CCC | CAG | GCA | AAC | TTG | CAC |
| Arg | Ser | Gly | Gly | Pro | Gln | Ala | Asn | Leu | His |

|  |  |  |  |  |  |  |  |  | 1652 |
|---|---|---|---|---|---|---|---|---|---|
| GAC | GCC | TGC | CAG | GGC | GAT | TCG | GGA | GGC | CCC |
| Asp | Ala | Cys | Gln | Gly | Asp | Ser | Gly | Gly | Pro |

|  |  |  |  |  |  |  |  |  | 1682 |
|---|---|---|---|---|---|---|---|---|---|
| CTG | GTG | TGT | CTG | AAC | GAT | GGC | CGC | ATG | ACT |
| Leu | Val | Cys | Leu | Asn | Asp | Gly | Arg | Met | Thr |

Figure 9f

TRIS-KRINGLE PA, OF FIG. (1a)

```
                                                    1712
TTG GTG GGC ATC ATC AGC TGG GGC CTG GGC
Leu Val Gly Ile Ile Ser Trp Gly Leu Gly

1742
TGT GGA CAG AAG GAT GTC CCG GGT GTG TAC
Cys Gly Gln Lys Asp Val Pro Gly Val Tyr

1772
ACA AAG GTT ACC AAC TAC CTA GAC TGG ATT
Thr Lys Val Thr Asn Tyr Leu Asp Trp Ile

1802
CGT GAC AAC ATG CGA CCG TGA CCAGGAACA
Arg Asp Asn Met Arg Pro End

1836
CCCGACTCCTCAAAAGCAAATGAGATCCGGATCC
```

Figure 9g

TRIS-KRINGLE PA, OF FIG. (1b)

```
                                                    31
GGATCCAGCAATC  ATG  GAT  GCA  ATG  AAG  AGA
               Met  Asp  Ala  Met  Lys  Arg

61
GGG  CTC  TGC  TGT  GTG  CTG  CTG  CTG  TGT  GGA
Gly  Leu  Cys  Cys  Val  Leu  Leu  Leu  Cys  Gly

91
GCA  GTC  TTC  GTT  TCG  CCC  AGC  CAG  GAA  ATC
Ala  Val  Phe  Val  Ser  Pro  Ser  Gln  Glu  Ile

121
CAT  GCC  CGA  TTC  AGA  AGA  GGA  GCC  AGA  TCT
His  Ala  Arg  Phe  Arg  Arg  Gly  Ala  Arg  Ser

151
TAC  CAA  GTG  ATC  TGC  AGA  GAT  GAA  AAA  ACG
Tyr  Gln  Val  Ile  Cys  Arg  Asp  Glu  Lys  Thr

181
CAG  ATG  ATA  TAC  CAG  CAA  CAT  CAG  TCA  TGG
Gln  Met  Ile  Tyr  Gln  Gln  His  Gln  Ser  Trp

211
CTG  CGC  CCT  GTG  CTC  AGA  AGC  AAC  CGG  GTG
Leu  Arg  Pro  Val  Leu  Arg  Ser  Asn  Arg  Val

241
GAA  TAT  TGC  TGG  TGC  AAC  AGT  GGC  AGG  GCA
Glu  Tyr  Cys  Trp  Cys  Asn  Ser  Gly  Arg  Ala
```

Figure 10

TRIS-KRINGLE PA, OF FIG. (1b)

```
                                                                    271
CAG  TGC  CAC  TCA  GTG  CCT  GTC  AAA  AGT  TGC
Gln  Cys  His  Ser  Val  Pro  Val  Lys  Ser  Cys

301
AGC  GAG  CCA  AGG  TGT  TTC  AAC  GGG  GGC  ACC
Ser  Glu  Pro  Arg  Cys  Phe  Asn  Gly  Gly  Thr

331
TGC  CAG  CAG  GCC  CTG  TAC  TTC  TCA  GAT  TTC
Cys  Gln  Gln  Ala  Leu  Tyr  Phe  Ser  Asp  Phe

361
GTG  TGC  CAG  TGC  CCC  GAA  GGA  TTT  GCT  GGG
Val  Cys  Gln  Cys  Pro  Glu  Gly  Phe  Ala  Gly

391
AAG  TGC  TGT  GAA  ATA  GAT  ACC  AGG  GCC  ACG
Lys  Cys  Cys  Glu  Ile  Asp  Thr  Arg  Ala  Thr

421
TGC  TAT  GAG  GGG  AAT  GGT  CAC  TTT  TAC  CGA
Cys  Tyr  Glu  Gly  Asn  Gly  His  Phe  Tyr  Arg

451
GGA  AAG  GCC  AGC  ACT  GAC  ACC  ATG  GGC  CGG
Gly  Lys  Ala  Ser  Thr  Asp  Thr  Met  Gly  Arg

481
CCC  TGC  CTG  CCC  TGG  AAC  TCT  GCC  ACT  GTC
Pro  Cys  Leu  Pro  Trp  Asn  Ser  Ala  Thr  Val
```

Figure 10a

TRIS-KRINGLE PA, OF FIG. (1b)

```
                                                        511
CTT  CAG  CAA  ACG  TAC  CAT  GCC  CAC  AGA  TCT
Leu  Gln  Gln  Thr  Tyr  His  Ala  His  Arg  Ser

541
GAT  GCT  CTT  CAG  CTG  CGC  CTG  GGG  AAA  CAT
Asp  Ala  Leu  Gln  Leu  Gly  Leu  Gly  Lys  His

571
AAT  TAC  TGC  AGG  AAC  CCA  GAC  AAC  CGG  AGG
Asn  Tyr  Cys  Arg  Asn  Pro  Asp  Asn  Arg  Arg

601
CGA  CCC  TGG  TGC  TAT  GTG  CAG  GTG  GGC  CTA
Arg  Pro  Trp  Cys  Tyr  Val  Gln  Val  Gly  Leu

631
AAG  CCG  CTT  GTC  CAA  GAG  TGC  ATG  GTG  CAT
Lys  Pro  Leu  Val  Gln  Glu  Cys  Met  Val  His

661
GAC  TGC  AGC  GAG  GGC  AAC  TCC  GAC  TGC  TAC
Asp  Cys  Ser  Glu  Gly  Asn  Ser  Asp  Cys  Tyr

691
GAG  GAC  CAG  GGC  ATC  AGC  TAC  AGG  GGC  ACG
Glu  Asp  Gln  Gly  Ile  Ser  Tyr  Arg  Gly  Thr

721
TGG  AGC  ACA  GCG  GAG  AGT  GGC  GCC  GAG  TGC
Trp  Ser  Thr  Ala  Glu  Ser  Gly  Ala  Glu  Cys
```

Figure 10b

TRIS-KRINGLE PA, OF FIG. (1b)

| | | | | | | | | | 751 |
|---|---|---|---|---|---|---|---|---|---|
| ACC | AAC | TGG | AAC | AGC | AGC | GCG | TTG | GCC | CAG |
| Thr | Asn | Trp | Asn | Ser | Ser | Ala | Leu | Ala | Gln |

| | | | | | | | | | 781 |
|---|---|---|---|---|---|---|---|---|---|
| AAG | CCC | TAC | AGC | GGG | CGG | AGG | CCA | GAC | GCC |
| Lys | Pro | Tyr | Ser | Gly | Arg | Arg | Pro | Asp | Ala |

| | | | | | | | | | 811 |
|---|---|---|---|---|---|---|---|---|---|
| ATC | AGG | CTG | GGC | CTG | GGG | AAC | CAC | AAC | TAC |
| Ile | Arg | Leu | Gly | Leu | Gly | Asn | His | Asn | Tyr |

| | | | | | | | | | 841 |
|---|---|---|---|---|---|---|---|---|---|
| TGC | AGA | AAC | CCA | GAT | CGA | GAC | TCA | AAG | CCC |
| Cys | Arg | Asn | Pro | Asp | Arg | Asp | Ser | Lys | Pro |

| | | | | | | | | | 871 |
|---|---|---|---|---|---|---|---|---|---|
| TGG | TGC | TAC | GTC | TTT | AAG | GCG | GGG | AAG | TAC |
| Trp | Cys | Tyr | Val | Phe | Lys | Ala | Gly | Lys | Tyr |

| | | | | | | | | | 901 |
|---|---|---|---|---|---|---|---|---|---|
| AGC | TCA | GAG | TTC | TGC | AGC | ACC | CCT | GCC | TGC |
| Ser | Ser | Glu | Phe | Cys | Ser | Thr | Pro | Ala | Cys |

| | | | | | | | | | 931 |
|---|---|---|---|---|---|---|---|---|---|
| TCT | GAG | GGA | AAC | AGT | GAC | TGC | TAC | TTT | GGG |
| Ser | Glu | Gly | Asn | Ser | Asp | Cys | Tyr | Phe | Gly |

| | | | | | | | | | 961 |
|---|---|---|---|---|---|---|---|---|---|
| AAT | GGG | TCA | GCC | TAC | CGT | GGC | ACG | CAC | AGC |
| Asn | Gly | Ser | Ala | Tyr | Arg | Gly | Thr | His | Ser |

Figure 10c

TRIS-KRINGLE PA, OF FIG. (1b)

```
                                                          991
CTC  ACC  GAG  TCG  GGT  GCC  TCC  TGC  CTC  CCG
Leu  Thr  Glu  Ser  Gly  Ala  Ser  Cys  Leu  Pro

1021
TGG  AAT  TCC  ATG  ATC  CTG  ATA  GGC  AAG  GTT
Trp  Asn  Ser  Met  Ile  Leu  Ile  Gly  Lys  Val

1051
TAC  ACA  GCA  CAG  AAC  CCC  AGT  GCC  CAG  GCA
Tyr  Thr  Ala  Gln  Asn  Pro  Ser  Ala  Gln  Ala

1081
CTG  GGC  CTG  GGC  AAA  CAT  AAT  TAC  TGC  CGG
Leu  Gly  Leu  Gly  Lys  His  Asn  Tyr  Cys  Arg

1111
AAT  CCT  GAT  GGG  GAT  GCC  AAG  CCC  TGG  TGC
Asn  Pro  Asp  Gly  Asp  Ala  Lys  Pro  Trp  Cys

1141
CAC  GTG  CTG  AAG  AAC  CGC  AGG  CTG  ACG  TGG
His  Val  Leu  Lys  Asn  Arg  Arg  Leu  Thr  Trp

1171
GAG  TAC  TGT  GAT  GTG  CCC  TCC  TGC  TCC  ACC
Glu  Tyr  Cys  Asp  Val  Pro  Ser  Cys  Ser  Thr

1201
TGC  GGC  CTG  AGA  CAG  TAC  AGC  CAG  CCT  CAG
Cys  Gly  Leu  Arg  Gln  Tyr  Ser  Gln  Pro  Gln
```

Figure 10d

TRIS-KRINGLE PA, OF FIG. (1b)

|     |     |     |     |     |     |     |     |     | 1231 |
|-----|-----|-----|-----|-----|-----|-----|-----|-----|------|
| TTT | CGC | ATC | AAA | GGA | GGG | CTC | TTC | GCC | GAC  |
| Phe | Arg | Ile | Lys | Gly | Gly | Leu | Phe | Ala | Asp  |

|     |     |     |     |     |     |     |     |     | 1261 |
|-----|-----|-----|-----|-----|-----|-----|-----|-----|------|
| ATC | GCC | TCC | CAC | CCC | TGG | CAG | GCT | GCC | ATC  |
| Ile | Ala | Ser | His | Pro | Trp | Gln | Ala | Ala | Ile  |

|     |     |     |     |     |     |     |     |     | 1291 |
|-----|-----|-----|-----|-----|-----|-----|-----|-----|------|
| TTT | GCC | AAG | CAC | AGG | AGG | TCG | CCC | GGA | GAG  |
| Phe | Ala | Lys | His | Arg | Arg | Ser | Pro | Gly | Glu  |

|     |     |     |     |     |     |     |     |     | 1321 |
|-----|-----|-----|-----|-----|-----|-----|-----|-----|------|
| CGG | TTC | CTG | TGC | GGG | GGC | ATA | CTC | ATC | AGC  |
| Arg | Phe | Leu | Cys | Gly | Gly | Ile | Leu | Ile | Ser  |

|     |     |     |     |     |     |     |     |     | 1351 |
|-----|-----|-----|-----|-----|-----|-----|-----|-----|------|
| TCC | TGC | TGG | ATT | CTC | TCT | GCC | GCC | CAC | TGC  |
| Ser | Cys | Trp | Ile | Leu | Ser | Ala | Ala | His | Cys  |

|     |     |     |     |     |     |     |     |     | 1381 |
|-----|-----|-----|-----|-----|-----|-----|-----|-----|------|
| TTC | CAG | GAG | AGG | TTT | CCG | CCC | CAC | CAC | CTG  |
| Phe | Gln | Glu | Arg | Phe | Pro | Pro | His | His | Leu  |

|     |     |     |     |     |     |     |     |     | 1411 |
|-----|-----|-----|-----|-----|-----|-----|-----|-----|------|
| ACG | GTG | ATC | TTG | GGC | AGA | ACA | TAC | CGG | GTG  |
| Thr | Val | Ile | Leu | Gly | Arg | Thr | Tyr | Arg | Val  |

|     |     |     |     |     |     |     |     |     | 1441 |
|-----|-----|-----|-----|-----|-----|-----|-----|-----|------|
| GTC | CCT | GGC | GAG | GAG | GAG | CAG | AAA | TTT | GAA  |
| Val | Pro | Gly | Glu | Glu | Glu | Gln | Lys | Phe | Glu  |

Figure 10e

TRIS-KRINGLE PA, OF FIG. (1b)

| | | | | | | | | | 1471 |
|---|---|---|---|---|---|---|---|---|---|
| GTC | GAA | AAA | TAC | ATT | GTC | CAT | AAG | GAA | TTC |
| Val | Glu | Lys | Tyr | Ile | Val | His | Lys | Glu | Phe |

| | | | | | | | | | 1501 |
|---|---|---|---|---|---|---|---|---|---|
| GAT | GAT | GAC | ACT | TAC | GAC | AAT | GAC | ATT | GCG |
| Asp | Asp | Asp | Thr | Tyr | Asp | Asn | Asp | Ile | Ala |

| | | | | | | | | | 1531 |
|---|---|---|---|---|---|---|---|---|---|
| CTG | CTG | CAG | CTG | AAA | TCG | GAT | TCG | TCC | CGC |
| Leu | Leu | Gln | Leu | Lys | Ser | Asp | Ser | Ser | Arg |

| | | | | | | | | | 1561 |
|---|---|---|---|---|---|---|---|---|---|
| TGT | GCC | CAG | GAG | AGC | AGC | GTG | GTC | CGC | ACT |
| Cys | Ala | Gln | Glu | Ser | Ser | Val | Val | Arg | Thr |

| | | | | | | | | | 1591 |
|---|---|---|---|---|---|---|---|---|---|
| GTG | TGC | CTT | CCC | CCG | GCG | GAC | CTG | CAG | CTG |
| Val | Cys | Leu | Pro | Pro | Ala | Asp | Leu | Gln | Leu |

| | | | | | | | | | 1621 |
|---|---|---|---|---|---|---|---|---|---|
| CCG | GAC | TGG | ACG | GAG | TGT | GAG | CTC | TCC | GGC |
| Pro | Asp | Trp | Thr | Glu | Cys | Glu | Leu | Ser | Gly |

| | | | | | | | | | 1651 |
|---|---|---|---|---|---|---|---|---|---|
| TAC | GGC | AAG | CAT | GAG | GCC | TTG | TCT | CCT | TTC |
| Tyr | Gly | Lys | His | Glu | Ala | Leu | Ser | Pro | Phe |

| | | | | | | | | | 1681 |
|---|---|---|---|---|---|---|---|---|---|
| TAT | TCG | GAG | CGG | CTG | AAG | GAG | GCT | CAT | GTC |
| Tyr | Ser | Glu | Arg | Leu | Lys | Glu | Ala | His | Val |

Figure 10f

TRIS-KRINGLE PA, OF FIG. (1b)

```
                                                          1711
AGA  CTG  TAC  CCA  TCC  AGC  CGC  TGC  ACA  TCA
Arg  Leu  Tyr  Pro  Ser  Ser  Arg  Cys  Thr  Ser

1741
CAA  CAT  TTA  CTT  AAC  AGA  ACA  GTC  ACC  GAC
Gln  His  Leu  Leu  Asn  Arg  Thr  Val  Thr  Asp

1771
AAC  ATG  CTG  TGT  GCT  GGA  GAC  ACT  CGG  AGC
Asn  Met  Leu  Cys  Ala  Gly  Asp  Thr  Arg  Ser

1801
GGC  GGG  CCC  CAG  GCA  AAC  TTG  CAC  GAC  GCC
Gly  Gly  Pro  Gln  Ala  Asn  Leu  His  Asp  Ala

1831
TGC  CAG  GGC  GAT  TCG  GGA  GGC  CCC  CTG  GTG
Cys  Gln  Gly  Asp  Ser  Gly  Gly  Pro  Leu  Val

1861
TGT  CTG  AAC  GAT  GGC  CGC  ATG  ACT  TTG  GTG
Cys  Leu  Asn  Asp  Gly  Arg  Met  Thr  Leu  Val

1891
GGC  ATC  ATC  AGC  TGG  GGC  CTG  GGC  TCT  GGA
Gly  Ile  Ile  Ser  Trp  Gly  Leu  Gly  Cys  Gly

1921
CAG  AAG  GAT  GTC  CCG  GGT  GTG  TAC  ACA  AAG
Gln  Lys  Asp  Val  Pro  Gly  Val  Tyr  Thr  Lys
```

Figure 10g

TRIS-KRINGLE PA, OF FIG. (1b)

```
                                                          1951
GTT  ACC  AAC  TAC  CTA  GAC  TGG  ATT  CGT  GAC
Val  Thr  Asn  Tyr  Leu  Asp  Trp  Ile  Arg  Asp

1981
AAC  ATG  CGA  CCG  TGA  CCAGGAACACCCGAC
Asn  Met  Arg  Pro  End

2009
TCCTCAAAAGCAAATGAGATCCGGATCC
```

Figure 10h

TRIS-KRINGLE PA, OF FIG. (1c)

```
                                                        31
GGATCCAGCAATC  ATG  GAT  GCA  ATG  AAG  AGA
               Met  Asp  Ala  Met  Lys  Arg

61
GGG  CTC  TGC  TGT  GTG  CTG  CTG  CTG  TGT  GGA
Gly  Leu  Cys  Cys  Val  Leu  Leu  Leu  Cys  Gly

91
GCA  GTC  TTC  GTT  TCG  CCC  AGC  CAG  GAA  ATC
Ala  Val  Phe  Val  Ser  Pro  Ser  Gln  Glu  Ile

121
CAT  GCC  CGA  TTC  AGA  AGA  GGA  GCC  AGA  TCT
His  Ala  Arg  Phe  Arg  Arg  Gly  Ala  Arg  Ser

151
TAC  CAA  GTG  ATC  TGC  AGA  GAT  GAA  AAA  ACG
Tyr  Gln  Val  Ile  Cys  Arg  Asp  Glu  Lys  Thr

181
CAG  ATG  ATA  TAC  CAG  CAA  CAT  CAG  TCA  TGG
Gln  Met  Ile  Tyr  Gln  Gln  His  Gln  Ser  Trp

211
CTG  CGC  CCT  GTG  CTC  AGA  AGC  AAC  CGG  GTG
Leu  Arg  Pro  Val  Leu  Arg  Ser  Asn  Arg  Val

241
GAA  TAT  TGC  TGG  TGC  AAC  AGT  GGC  AGG  GCA
Glu  Tyr  Cys  Trp  Cys  Asn  Ser  Gly  Arg  Ala
```

Figure 11

TRIS-KRINGLE PA, OF FIG. (1c)

| | | | | | | | | | 271 |
|---|---|---|---|---|---|---|---|---|---|
| CAG | TGC | CAC | TCA | GTG | CCT | GTC | AAA | AGT | TGC |
| Gln | Cys | His | Ser | Val | Pro | Val | Lys | Ser | Cys |

| | | | | | | | | | 301 |
|---|---|---|---|---|---|---|---|---|---|
| AGC | GAG | CCA | AGG | TGT | TTC | AAC | GGG | GGC | ACC |
| Ser | Glu | Pro | Arg | Cys | Phe | Asn | Gly | Gly | Thr |

| | | | | | | | | | 331 |
|---|---|---|---|---|---|---|---|---|---|
| TGC | CAG | CAG | GCC | CTG | TAC | TTC | TCA | GAT | TTC |
| Cys | Gln | Gln | Ala | Leu | Tyr | Phe | Ser | Asp | Phe |

| | | | | | | | | | 361 |
|---|---|---|---|---|---|---|---|---|---|
| GTG | TGC | CAG | TGC | CCC | GAA | GGA | TTT | GCT | GGG |
| Val | Cys | Gln | Cys | Pro | Glu | Gly | Phe | Ala | Gly |

| | | | | | | | | | 391 |
|---|---|---|---|---|---|---|---|---|---|
| AAG | TGC | TGT | GAA | ATA | GAT | ACC | AGG | GCC | ACG |
| Lys | Cys | Cys | Glu | Ile | Asp | Thr | Arg | Ala | Thr |

| | | | | | | | | | 421 |
|---|---|---|---|---|---|---|---|---|---|
| TGC | TAC | GAG | GAC | CAG | GGC | ATC | AGC | TAC | AGG |
| Cys | Tyr | Glu | Asp | Gln | Gly | Ile | Ser | Tyr | Arg |

| | | | | | | | | | 451 |
|---|---|---|---|---|---|---|---|---|---|
| GGC | ACG | TGG | AGC | ACA | GCG | GAG | AGT | GGC | GCC |
| Gly | Thr | Trp | Ser | Thr | Ala | Glu | Ser | Gly | Ala |

| | | | | | | | | | 481 |
|---|---|---|---|---|---|---|---|---|---|
| GAG | TGC | ACC | AAC | TGG | AAC | AGC | AGC | GCG | TTG |
| Glu | Cys | Thr | Asn | Trp | Asn | Ser | Ser | Ala | Leu |

Figure 11a

TRIS-KRINGLE PA, OF FIG. (1c)

|     |     |     |     |     |     |     |     |     | 511 |
| --- | --- | --- | --- | --- | --- | --- | --- | --- | --- |
| GCC | CAG | AAG | CCC | TAC | AGC | GGG | CGG | AGG | CCA |
| Ala | Gln | Lys | Pro | Tyr | Ser | Gly | Arg | Arg | Pro |

|     |     |     |     |     |     |     |     |     | 541 |
| --- | --- | --- | --- | --- | --- | --- | --- | --- | --- |
| GAC | GCC | ATC | AGG | CTG | GGC | CTG | GGG | AAC | CAC |
| Asp | Ala | Ile | Arg | Leu | Gly | Leu | Gly | Asn | His |

|     |     |     |     |     |     |     |     |     | 571 |
| --- | --- | --- | --- | --- | --- | --- | --- | --- | --- |
| AAC | TAC | TGC | AGA | AAC | CCA | GAT | CGA | GAC | TCA |
| Asn | Tyr | Cys | Arg | Asn | Pro | Asp | Arg | Asp | Ser |

|     |     |     |     |     |     |     |     |     | 601 |
| --- | --- | --- | --- | --- | --- | --- | --- | --- | --- |
| AAG | CCC | TGG | TGC | TAC | GTC | TTT | AAG | GCG | GGG |
| Lys | Pro | Trp | Cys | Tyr | Val | Phe | Lys | Ala | Gly |

|     |     |     |     |     |     |     |     |     | 631 |
| --- | --- | --- | --- | --- | --- | --- | --- | --- | --- |
| AAG | TAC | AGC | TCA | GAG | TTC | TGC | AGC | ACC | CCT |
| Lys | Tyr | Ser | Ser | Glu | Phe | Cys | Ser | Thr | Pro |

|     |     |     |     |     |     |     |     |     | 661 |
| --- | --- | --- | --- | --- | --- | --- | --- | --- | --- |
| GCC | TGC | TCT | GAG | GGA | AAC | AGT | GAC | TGC | TAC |
| Ala | Cys | Ser | Glu | Gly | Asn | Ser | Asp | Cys | Tyr |

|     |     |     |     |     |     |     |     |     | 691 |
| --- | --- | --- | --- | --- | --- | --- | --- | --- | --- |
| TTT | GGG | AAT | GGG | TCA | GCC | TAC | CGT | GGC | ACG |
| Phe | Gly | Asn | Gly | Ser | Ala | Tyr | Arg | Gly | Thr |

|     |     |     |     |     |     |     |     |     | 721 |
| --- | --- | --- | --- | --- | --- | --- | --- | --- | --- |
| CAC | AGC | CTC | ACC | GAG | TCG | GGT | GCC | TCC | TGC |
| His | Ser | Leu | Thr | Glu | Ser | Gly | Ala | Ser | Cys |

Figure 11b

TRIS-KRINGLE PA, OF FIG. (1c)

```
                                                        751
CTC  CCG  TGG  AAT  TCC  ATG  ATC  CTG  ATA  GGC
Leu  Pro  Trp  Asn  Ser  Met  Ile  Leu  Ile  Gly

781
AAG  GTT  TAC  ACA  GCA  CAG  AAC  CCC  AGT  GCC
Lys  Val  Tyr  Thr  Ala  Gln  Asn  Pro  Ser  Ala

811
CAG  GCA  CTG  GGC  CTG  GGC  AAA  CAT  AAT  TAC
Gln  Ala  Leu  Gly  Leu  Gly  Lys  His  Asn  Tyr

841
TGC  CGG  AAT  CCT  GAT  GGG  GAT  GCC  AAG  CCC
Cys  Arg  Asn  Pro  Asp  Gly  Asp  Ala  Lys  Pro

871
TGG  TGC  CAC  GTG  CTG  AAG  AAC  CGC  AGG  CTG
Trp  Cys  His  Val  Leu  Lys  Asn  Arg  Arg  Leu

901
ACG  TGG  GAG  TAC  TGT  GAT  GTG  CCC  TCC  TGC
Thr  Trp  Glu  Tyr  Cys  Asp  Val  Pro  Ser  Cys

931
TCC  GAG  GGC  AAC  TCC  GAC  TGC  TAT  GAG  GGG
Ser  Glu  Gly  Asn  Ser  Asp  Cys  Tyr  Glu  Gly

961
AAT  GGT  CAC  TTT  TAC  CGA  GGA  AAG  CCC  AGC
Asn  Gly  His  Phe  Tyr  Arg  Gly  Lys  Ala  Ser
```

Figure 11c

TRIS-KRINGLE PA, OF FIG. (1c)

|     |     |     |     |     |     |     |     |     | 991 |
| --- | --- | --- | --- | --- | --- | --- | --- | --- | --- |
| ACT | GAC | ACC | ATG | GGC | CGG | CCC | TGC | CTG | CCC |
| Thr | Asp | Thr | Met | Gly | Arg | Pro | Cys | Leu | Pro |

|     |     |     |     |     |     |     |     |     | 1021 |
| --- | --- | --- | --- | --- | --- | --- | --- | --- | --- |
| TGG | AAC | TCT | GCC | ACT | GTC | CTT | CAG | CAA | ACG |
| Trp | Asn | Ser | Ala | Thr | Val | Leu | Gln | Gln | Thr |

|     |     |     |     |     |     |     |     |     | 1051 |
| --- | --- | --- | --- | --- | --- | --- | --- | --- | --- |
| TAC | CAT | GCC | CAC | AGA | TCT | GAT | GCT | CTT | CAG |
| Tyr | His | Ala | His | Arg | Ser | Asp | Ala | Leu | Gln |

|     |     |     |     |     |     |     |     |     | 1081 |
| --- | --- | --- | --- | --- | --- | --- | --- | --- | --- |
| CTG | GGC | CTG | GGG | AAA | CAT | AAT | TAC | TGC | AGG |
| Leu | Gly | Leu | Gly | Lys | His | Asn | Tyr | Cys | Arg |

|     |     |     |     |     |     |     |     |     | 1111 |
| --- | --- | --- | --- | --- | --- | --- | --- | --- | --- |
| AAC | CCA | GAC | AAC | CGG | AGG | CGA | CCC | TGG | TGC |
| Asn | Pro | Asp | Asn | Arg | Arg | Arg | Pro | Trp | Cys |

|     |     |     |     |     |     |     |     |     | 1141 |
| --- | --- | --- | --- | --- | --- | --- | --- | --- | --- |
| TAT | GTG | CAG | GTG | GGC | CTA | AAG | CCG | CTT | GTC |
| Tyr | Val | Gln | Val | Gly | Leu | Lys | Pro | Leu | Val |

|     |     |     |     |     |     |     |     |     | 1171 |
| --- | --- | --- | --- | --- | --- | --- | --- | --- | --- |
| CAA | GAG | TGC | ATG | GTG | CAT | GAC | TGC | TCC | ACC |
| Gln | Glu | Cys | Met | Val | His | Asp | Cys | Ser | Thr |

|     |     |     |     |     |     |     |     |     | 1201 |
| --- | --- | --- | --- | --- | --- | --- | --- | --- | --- |
| TGC | GGC | CTG | AGA | CAG | TAC | AGC | CAG | CCT | CAG |
| Cys | Gly | Leu | Arg | Gln | Tyr | Ser | Gln | Pro | Gln |

Figure 11d

TRIS-KRINGLE PA, OF FIG. (1c)

|     |     |     |     |     |     |     |     |     | 1231 |
| --- | --- | --- | --- | --- | --- | --- | --- | --- | ---- |
| TTT | CGC | ATC | AAA | GGA | GGG | CTC | TTC | GCC | GAC  |
| Phe | Arg | Ile | Lys | Gly | Gly | Leu | Phe | Ala | Asp  |

|     |     |     |     |     |     |     |     |     | 1261 |
| --- | --- | --- | --- | --- | --- | --- | --- | --- | ---- |
| ATC | GCC | TCC | CAC | CCC | TGG | CAG | GCT | GCC | ATC  |
| Ile | Ala | Ser | His | Pro | Trp | Gln | Ala | Ala | Ile  |

|     |     |     |     |     |     |     |     |     | 1291 |
| --- | --- | --- | --- | --- | --- | --- | --- | --- | ---- |
| TTT | GCC | AAG | CAC | AGG | AGG | TCG | CCC | GGA | GAG  |
| Phe | Ala | Lys | His | Arg | Arg | Ser | Pro | Gly | Glu  |

|     |     |     |     |     |     |     |     |     | 1321 |
| --- | --- | --- | --- | --- | --- | --- | --- | --- | ---- |
| CGG | TTC | CTG | TGC | GGG | GGC | ATA | CTC | ATC | AGC  |
| Arg | Phe | Leu | Cys | Gly | Gly | Ile | Leu | Ile | Ser  |

|     |     |     |     |     |     |     |     |     | 1351 |
| --- | --- | --- | --- | --- | --- | --- | --- | --- | ---- |
| TCC | TGC | TGG | ATT | CTC | TCT | GCC | GCC | CAC | TGC  |
| Ser | Cys | Trp | Ile | Leu | Ser | Ala | Ala | His | Cys  |

|     |     |     |     |     |     |     |     |     | 1381 |
| --- | --- | --- | --- | --- | --- | --- | --- | --- | ---- |
| TTC | CAG | GAG | AGG | TTT | CCG | CCC | CAC | CAC | CTG  |
| Phe | Gln | Glu | Arg | Phe | Pro | Pro | His | His | Leu  |

|     |     |     |     |     |     |     |     |     | 1411 |
| --- | --- | --- | --- | --- | --- | --- | --- | --- | ---- |
| ACG | GTG | ATC | TTG | GGC | AGA | ACA | TAC | CGG | GTG  |
| Thr | Val | Ile | Leu | Gly | Arg | Thr | Tyr | Arg | Val  |

|     |     |     |     |     |     |     |     |     | 1441 |
| --- | --- | --- | --- | --- | --- | --- | --- | --- | ---- |
| GTC | CCT | GGC | GAG | GAG | GAG | CAG | AAA | TTT | GAA  |
| Val | Pro | Gly | Glu | Glu | Glu | Gln | Lys | Phe | Glu  |

Figure 11e

TRIS-KRINGLE PA, OF FIG. (1c)

|     |     |     |     |     |     |     |     |     | 1471 |
| --- | --- | --- | --- | --- | --- | --- | --- | --- | --- |
| GTC | GAA | AAA | TAC | ATT | GTC | CAT | AAG | GAA | TTC |
| Val | Glu | Lys | Tyr | Ile | Val | His | Lys | Glu | Phe |

|     |     |     |     |     |     |     |     |     | 1501 |
| --- | --- | --- | --- | --- | --- | --- | --- | --- | --- |
| GAT | GAT | GAC | ACT | TAC | GAC | AAT | GAC | ATT | GCG |
| Asp | Asp | Asp | Thr | Tyr | Asp | Asn | Asp | Ile | Ala |

|     |     |     |     |     |     |     |     |     | 1531 |
| --- | --- | --- | --- | --- | --- | --- | --- | --- | --- |
| CTG | CTG | CAG | CTG | AAA | TCG | GAT | TCG | TCC | CGC |
| Leu | Leu | Gln | Leu | Lys | Ser | Asp | Ser | Ser | Arg |

|     |     |     |     |     |     |     |     |     | 1561 |
| --- | --- | --- | --- | --- | --- | --- | --- | --- | --- |
| TGT | GCC | CAG | GAG | AGC | AGC | GTG | GTC | CGC | ACT |
| Cys | Ala | Gln | Glu | Ser | Ser | Val | Val | Arg | Thr |

|     |     |     |     |     |     |     |     |     | 1591 |
| --- | --- | --- | --- | --- | --- | --- | --- | --- | --- |
| GTG | TGC | CTT | CCC | CCG | GCG | GAC | CTG | CAG | CTG |
| Val | Cys | Leu | Pro | Pro | Ala | Asp | Leu | Gln | Leu |

|     |     |     |     |     |     |     |     |     | 1621 |
| --- | --- | --- | --- | --- | --- | --- | --- | --- | --- |
| CCG | GAC | TGG | ACG | GAG | TGT | GAG | CTC | TCC | GGC |
| Pro | Asp | Trp | Thr | Glu | Cys | Glu | Leu | Ser | Gly |

|     |     |     |     |     |     |     |     |     | 1651 |
| --- | --- | --- | --- | --- | --- | --- | --- | --- | --- |
| TAC | GGC | AAG | CAT | GAG | GCC | TTG | TCT | CCT | TTC |
| Tyr | Gly | Lys | His | Glu | Ala | Leu | Ser | Pro | Phe |

|     |     |     |     |     |     |     |     |     | 1681 |
| --- | --- | --- | --- | --- | --- | --- | --- | --- | --- |
| TAT | TCG | GAG | CGG | CTG | AAG | GAG | GCT | CAT | GTC |
| Tyr | Ser | Glu | Arg | Leu | Lys | Glu | Ala | His | Val |

Figure 11f

TRIS-KRINGLE PA, OF FIG. (1c)

|     |     |     |     |     |     |     |     |     | 1711 |
| --- | --- | --- | --- | --- | --- | --- | --- | --- | --- |
| AGA | CTG | TAC | CCA | TCC | AGC | CGC | TGC | ACA | TCA |
| Arg | Leu | Tyr | Pro | Ser | Ser | Arg | Cys | Thr | Ser |

|     |     |     |     |     |     |     |     |     | 1741 |
| --- | --- | --- | --- | --- | --- | --- | --- | --- | --- |
| CAA | CAT | TTA | CTT | AAC | AGA | ACA | GTC | ACC | GAC |
| Gln | His | Leu | Leu | Asn | Arg | Thr | Val | Thr | Asp |

|     |     |     |     |     |     |     |     |     | 1771 |
| --- | --- | --- | --- | --- | --- | --- | --- | --- | --- |
| AAC | ATG | CTG | TGT | GCT | GGA | GAC | ACT | CGG | AGC |
| Asn | Met | Leu | Cys | Ala | Gly | Asp | Thr | Arg | Ser |

|     |     |     |     |     |     |     |     |     | 1801 |
| --- | --- | --- | --- | --- | --- | --- | --- | --- | --- |
| GGC | GGG | CCC | CAG | GCA | AAC | TTG | CAC | GAC | GCC |
| Gly | Gly | Pro | Gln | Ala | Asn | Leu | His | Asp | Ala |

|     |     |     |     |     |     |     |     |     | 1831 |
| --- | --- | --- | --- | --- | --- | --- | --- | --- | --- |
| TGC | CAG | GGC | GAT | TCG | GGA | GGC | CCC | CTG | GTG |
| Cys | Gln | Gly | Asp | Ser | Gly | Gly | Pro | Leu | Val |

|     |     |     |     |     |     |     |     |     | 1861 |
| --- | --- | --- | --- | --- | --- | --- | --- | --- | --- |
| TGT | CTG | AAC | GAT | GGC | CGC | ATG | ACT | TTG | GTG |
| Cys | Leu | Asn | Asp | Gly | Arg | Met | Thr | Leu | Val |

|     |     |     |     |     |     |     |     |     | 1891 |
| --- | --- | --- | --- | --- | --- | --- | --- | --- | --- |
| GGC | ATC | ATC | AGC | TGG | GGC | CTG | GGC | TGT | GGA |
| Gly | Ile | Ile | Ser | Trp | Gly | Leu | Gly | Cys | Gly |

|     |     |     |     |     |     |     |     |     | 1921 |
| --- | --- | --- | --- | --- | --- | --- | --- | --- | --- |
| CAG | AAG | GAT | GTC | CCG | GGT | GTG | TAC | ACA | AAG |
| Gln | Lys | Asp | Val | Pro | Gly | Val | Tyr | Thr | Lys |

Figure 11g

TRIS-KRINGLE PA, OF FIG. (1c)

```
                                                      1951
GTT  ACC  AAC  TAC  CTA  GAC  TGG  ATT  CGT  GAC
Val  Thr  Asn  Tyr  Leu  Asp  Trp  Ile  Arg  Asp

1981
AAC  ATG  CGA  CCG  TGA  CCAGGAACACCCGAC
Asn  Met  Arg  Pro  End

2009
TCCTCAAAAGCAAATGAGATC CGGATCC
```

Figure 11h

A. EXPRESSION VECTOR: Hybrid A

B. EXPRESSION VECTOR: Hybrid B

PROCESS FOR TREATING THROMBOSIS BY ADMINISTERING POLY-KRINGLE PLASMINOGEN ACTIVATOR

This is a division of application ser. No. 07/436,528 filed Nov. 14, 1989, now U.S. Pat. No. 4,997,766, which is a Division of Ser. No. 06/884,835 filed on July 11, 1986, now U.S. Pat. No. 4,916,071, which is a continuation-in-part of Ser. No. 766,163, filed Aug. 14, 1985, which is now abandoned.

BACKGROUND OF THE INVENTION

Plasminogen activators are a class of serine proteases that convert plasminogen into plasmin. Plasmin degrades the fibrin matrix of blood clots, thereby restoring the hemodynamic condition of an open vascular system after an internal vascular accident has produced thrombosis or thromboembolism. Vascular disease states involving partial or total blockage of blood vessels which are amenable to treatment with plasminogen activators include stroke, pulmonary embolism, myocardial infarction, as well as deep vein and peripheral artery obstructions.

There are two immunologically distinct types of plasminogen activators found in human plasma and other body fluids—the urokinase-type plasminogen activator (u-PA; $M_r$, 55,000) and the tissue-type plasminogen activator (t-PA; $M_r$, 68,000). The activity of the tissue-type plasminogen activator is potentiated by fibrin. The enzyme acts at the site of a thrombus and demonstrates a higher affinity for fibrin than does the urokinase-type plasminogen activator (Haylaeris et al., J. Biol. Chem., 257, 2912, 1982). Therefore, the tissue-type plasminogen activator is considered to be the physiologically relevant thrombolytic agent.

Both activators, u-PA and t-PA, share the following common features: 1) they are synthesized as single chain proenzymes which can be cleaved by plasmin or trypsin, without disrupting their disulfide linked two-chain molecular structure. Upon reduction, each plasminogen activator breaks down into a heavy and a light chain ($M_r$ 33,000 for u-PA; $M_r$ 35,000 for t-PA); 2) both enzymes are serine proteases which can be inactivated by serine-specific reagents such as diisopropyl fluorophosphate; and 3) both enzymes contain a triple disulfide-linked sequence of amino acids which form a loop or kringle in the molecule. Urokinase plasminogen activator has a single kringle. Tissue plasminogen activator has two kringles connected by a hexapeptide linker sequence. These kringles are believed to be responsible for binding of the enzymes to fibrin (Thorsen, Biochem. Biophys. Acta., 393, 55, 1975).

The DNA sequence analysis and the amino acid sequence of t-PA is disclosed by Pennica et al., Nature, 301, 214, (1983), Ny et al., Proc. Natl. Acad. Sci. U.S.A. 81 5355 (1984) and European Patent Application 93,619 to Genentech Inc. The DNA sequence analysis and the amino acid sequence of u-PA is disclosed in European Patent Application 92,182 to Genentech Inc. and urokinase cDNA is discussed by Verde et al., Proc. Natl. Acad. Sci. U.S.A. 81 4727 (1984).

DESCRIPTION OF THE INVENTION

In accordance with this invention there is provided a group of hybrid, third generation, plasminogen activators containing plural, heterologous polypeptide kringles. The polypeptides of this invention may contain from 2 to 6 kringles. By heterologous kringles, applicants mean the polypeptide product contains at least one kringle corresponding to that found in a different, naturally-occurring source or an additional kringle structure common to and in addition to those found in a native plasminogen activator. It is understood that where a common kringle structure is to be added to a native plasminogen activator to produce the hybrid plasminogen activators of this invention, the DNA is chemically synthesized and the DNA codon usage for production of that common kringle must differ from that found in the DNA coding sequence for the native plasminogen activator to avoid recombination (looping out) while generating the desired amino acid sequence of the native kringle. The kringles present in the hybrid plasminogen activators of this invention, although separately sharing areas of homology, are heterologous in nature and as a result thereof, the plasminogen activators of this invention differ in their kringle combination from any found in native plasminogen activators, either in amino acid sequence, number and/or size. In addition, this invention provides the genes coding for the hybrid plasminogen activators and key fragments thereof, expression vectors for DNA production of the complete polypeptides as well as key fragments thereof, microorganisms or cell cultures transformed with the expression vectors and a method for using the hybrid plasminogen activators.

A kringle is a triple looped polypeptide structure formed by three disulfide bonds. Kringles vary in length from about 79 to 82 amino acid groups. A high degree of sequence homology is shared among the single kringle of human urokinase (Gunzler et al., Hoppe-Seyler's Z. Physiol. Chem. 363, 1155, 1982), the two kringles of human tissue plasminogen activator (Pennica, et al. Nature, 301, 214, 1983), the two kringles of human prothrombin (Walz et al., Proc. Nat'l. Acad. Sci. USA., 74, 1969, 1977), and the five kringles of human plasminogen (Sottrup-Jensen et al., in Progress in Chemical Fibrinolysis and Thrombolysis (eds. Davidson et al.), 3, 191, 1978). The relative positions of the six cysteines involved in the intra-kringle disulfide bridges are conserved in all kringles. The term, kringle(s) used in this application may be taken to mean any of such structure(s) in the above mentioned proteins. It is also understood that polymorphic forms in the kringle region of these proteins may exist in nature where one or more amino acids may be added, deleted or substituted. Similar changes in a protein may also be brought about in vitro with the advent of the present day technology of point mutation of the gene or by chemical synthesis of the gene with any desired sequence. These modified structure(s) are therefore also included in the term, kringle(s), used in this application.

The following description specifically illustrates the production of a triple kringle (tris-kringle) plasminogen activator, as well as a tetra-kringle plasminogen activator. The methods employed are representative of those applicable to the production of the other polypeptides of this invention.

The tris-kringle plasminogen activators of this invention, as constructed by recombinant DNA techniques from appropriate genetic coding sequences of urokinase and t-PA clones, offer the advantages of increased stability, increased binding affinity for fibrin and improved half-life in vivo when compared to either of the native plasminogen activators. These properties of the tris-kringle plasminogen activators provide improved biological potency and improved shelf life. The tris-kringle-PA molecule is easier to handle during production and purification than native t-PA because the latter polypeptide, as found in culture fluids and various purification stages, is accompanied by low molecular weight, heavy and light chain fragments. The tetra-kringle plasminogen activator as well as the other poly-kringle plasminogen activators share these properties.

The tris-kringle plasminogen activator of this invention is constructed by combining the N-terminal portion of urokinase through its single kringle region with that portion of t-PA beginning at or before the beginning of the double kringle region via a suitable linker. The single kringle of urokinase is known to precede the glycine residue at amino acid position number 131. The double kringle of t-PA is known to begin at the cysteine following a threonine residue at position number 91. Thus, the N-terminal portion of urokinase terminated at the glycine residue at number 131 is joined, optionally through a suitable linker mimicking the hexapeptide link between the two kringles of t-PA, to a t-PA molecule from which the first 91 N-terminal amino acids have been deleted. The resulting hybrid molecule is larger than t-PA by 46 amino acid residues providing a protein of about 73,000 M.W. (t-PA has a molecular weight of 68,000) depending upon the specific linker employed. Similarly, the single kringle of urokinase (UKKaa50-131), in conjunction with a kringle linker, is inserted into the t-PA polymer between amino acids 91-92 or 261-262 to afford two different genes for production of tris-kringle plasminogen activators. Similarly, and by standard techniques, the u-PA kringle may be inserted, with appropriate linkers, between the two t-PA kringles. In addition, the kringles found in prothrombin or plasminogen may be isolated and inserted in any of the position of t-PA mentioned above. The construction of any of the poly-kringle plasminogen activators of this invention follows the same basic plan of isolating single or double kringle region from the protein mentioned and inserting them into the backbone of the t-PA molecule.

The kringle linkers employed to join the single kringle portion of urokinase (UKK) to the double kringle region of t-PA (t-PK1 and t-PK2) is a polypeptide containing 6 to 10 natural amino acid moieties. Preferably the kringle linker is selected to maintain a similar spatial arrangement to that which exists between the two kringles of t-PA. As such, the preferred linker is L-Ser-L-Glu-Gly-L-Asn-L-Ser-L-Asp because it is identical to that joining t-PK1 to t-PK2 in t-PA. However, the hexapeptide L-Thr-L-Asp-L-Ala-L-Glu-L-Thr-L-Glu represents another applicable hexapeptide linker and any combination of L-Ala, Gly, L-Ser, L-Glu, L-Thr and L-Asp may be employed on the N-terminal or C-terminal ends of the hexapeptide linker to provide a more open structure as a hepta-, octa-, nona- or decapeptide link between the t-PA kringles and the UK kringle. Other linkers will be obvious to the chemist. For simplicity, the kringle linker specifically mentioned throughout the rest of this application is limited to the preferred linker referred to above.

The tris-kringle plasminogen activators are produced by limited digestion of urokinase and t-PA coding sequences with selected restriction enzymes to afford the desired u-PA and t-PA fragments. The fragments are isolated by fractionation on agarose or acrylamide gels, ligated together and introduced into an appropriate vector or vectors for cloning and subsequent expression.

DESCRIPTION OF THE DRAWINGS

FIGS. 9A–9g present the DNA sequence of the gene coding for the product of FIG. 1(a) with reference to the urokinase signal peptide region (20 amino acids), the UKK region (amino acids 1-131 of urokinase), the hexapeptide linker and the remaining portion of the t-PA molecule (amino acids 92-527).

FIGS. 10A–10h present the DNA sequence of the gene coding for the product of FIG. 1(b) with reference to the t-PA signal peptide (35 amino acids) the N-terminal portion of t-PA (amino acids 1-91), the UKK (amino acids 50-131 of urokinase), the hexapeptide linker and the C-terminal portion of t-PA (amino acids 92-527).

FIGS. 11A–11h presents the DNA sequence of the gene coding for the product of FIG. 1(c) with reference to the t-PA signal peptide (35 amino acids), the N-terminal portion of t-PA (amino acids 1-261), the hexapeptide linker, the UKK (amino acids 50-131 of urokinase) and the C-terminal portion of t-PA (amino acids 262-527).

Figure 1:
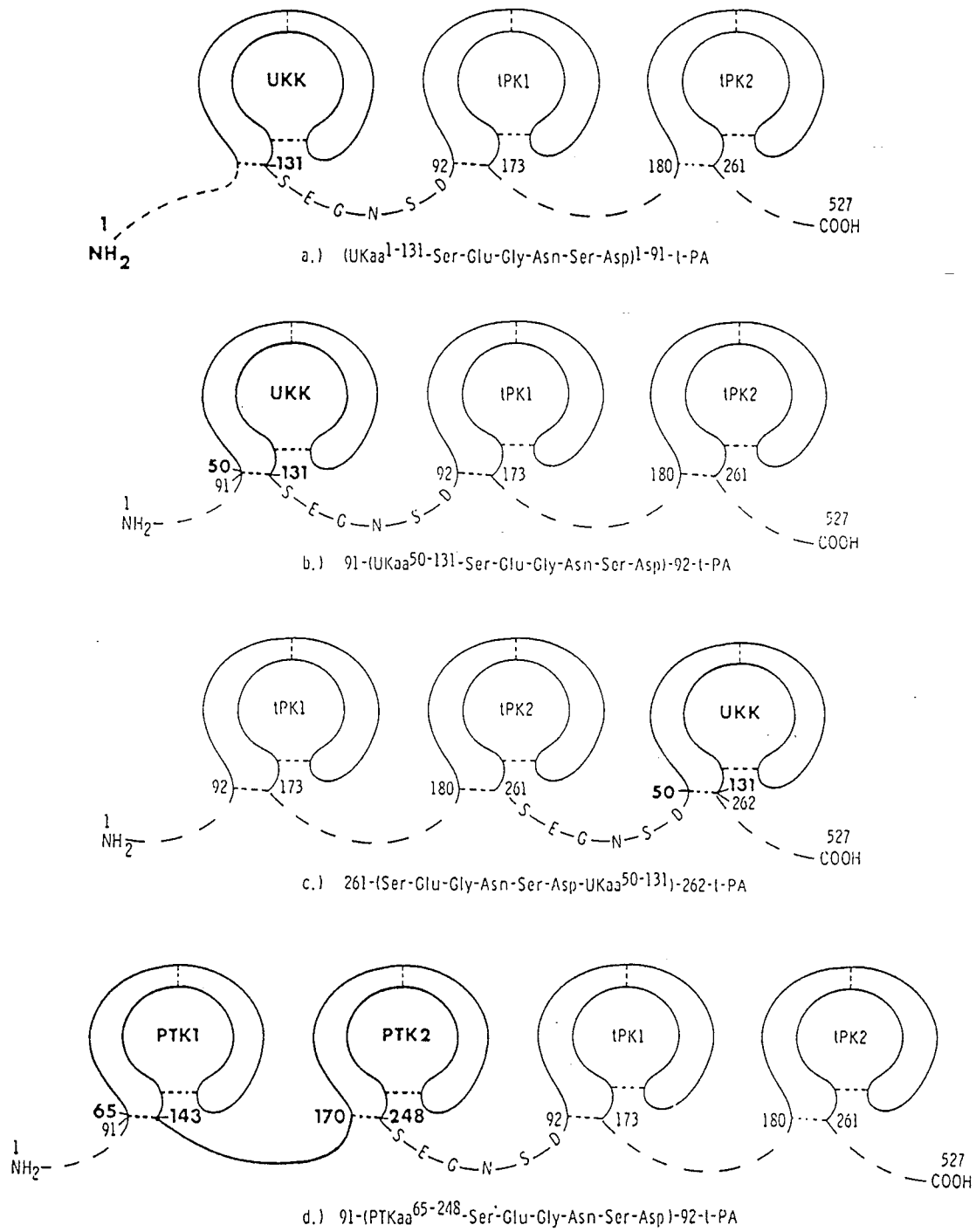
FIG. 1 presents schematic configurational drawings of three tris-kringle plasminogen activators and one tetra-kringle plasminogen activator produced by the methods disclosed in this application. The darkened portion of the depicted structures 1 (a–c) defines that portion of urokinase containing the urokinase kringle (UKK). The darkened portion of structure 1(d) defines the double kringle region of prothrombin (PTK1 and PTK2). The abbreviations tPK1 and tPK2 define the tissue plasminogen acivator kringle 1 and 2, respectively.

METHODS AND MATERIALS a) Enzymic Reactions: The restriction and DNA modifying enzymes were obtained from New England Biolabs Inc., Beverly, Mass. or International Biotechnologies Inc., New Heaven, Conn. A typical restriction enzyme reaction was performed in a total volume of 50 μl following the procedure(s) recommended by the supplier of the enzyme.

A ligation reaction for the sticky end DNA is typically performed at 15° C. overnight in a buffered 20 μl solution containing 100-200 ng DNA and 400 units of T4 DNA ligase (N. E. Biolabs.). For blunt end ligation, 4 units of T4 RNA ligase (N. E. Biolabs.) are included in the above reaction mixture. (Goodman, H. M., and MacDonald, R. J., Method. Enzymol. 68, 75, 1979). The buffer solution used is prepared as a stock 10X solution; 0.5 m Tris ®.HCl (pH 7.6), 0.1M $MgCl_2$ and 0.1M DTT (dithiothreitol).

b) Synthesis of Oligonucleotides: All the oligonucleotides mentioned in this application were synthesized by the phosphotriester method (Crea et al., Proc. Nat'l. Acad. Sci. (USA) 75, 5765, 1978) using the Gene Machine model 380A (Applied Biosystems Inc., Foster city, Cal.). Before their use in ligation reactions, the oligomers were phosphorylated at the 5' end in a volume of 50 μl containing 200-500 ng DNA, 10 units of T4 DNA kinase, 0.5 mM ATP and kinase buffer (0.05M Tris.HCl, pH 7.6, 10 mM $MgCl_2$, 5 mM DTT) and incubated at 37° C. for ½ hour. For use as hybridization probes, oligomers were radiolabeled with 100 μCi gamma $^{32}P$-ATP (5,000 $C_i$/mmol, Amersham, Arlington Heights, Ill.) following the procedure of Maxam, A. M. and Gilbert, W. Method Enzymol. 65, 499 (1980).

c) Isolation of DNA Fragments DNA fragments were first separated by electrophoresis through 0.5-1.5% agarose gel. Electrophoresis is carried out at about 100 volts for 2-4 hours in Tris-Borate-EDTA (TBE) buffer (0.089M Tris, 0.089M boric acid, 2 mM EDTA, pH 8.0). DNA bands are visualized under UV light by staining the gel in 0.5 μg/ml ethidium bromide solution (Sharp et al. Biochem. 12, 3055, 1973). The agarose containing the DNA band is cut out with a razor. The DNA is electroeluted from the gel. (Maniatis et al. Molecular Cloning, a Laboratory Manual, p. 164, 1982). The DNA is further purified by passing it through an Elutip-d ® column (Schleicher and Schuell, Keene, N.H.). The DNA is precipitated with ethanol. After centrifugation in an Eppendorf microfuge for 15 minutes, the pellet is washed once with 70% ethanol, dried under vacuum and dissolved in 50 μl deionized water.

d) Miniplasmid DNA Preparation: About 2 ml of LB (Luria Bertani) medium containing appropriate antibiotics is inoculated with a single bacterial colony and is incubated at 37° C. overnight with vigorous shaking. About 1.5 ml of the culture medium is used to isolate plasmid DNA by the boiling method described in Maniatis et al., loc. cit. p. 366. The rest of the culture is stored in 15% glycerol at −20° C. for later use. The DNA is dissolved in 40 μl $H_2O$ containing 10 μg RNAse /ml. About 8 μl is sufficient for one restriction enzyme analysis.

e) Large Scale Preparation of Plasmid DNA: Typically, one liter of LB medium is inoculated with a single bacterial colony. After amplification of the plasmid DNA with chloramphenicol, the bacterial cells are harvested and lysed according to the boiling method (Holmes, D. S. and Quigley, M. Anal Biochem. 114, 193, 1981). The plasmid DNA is further purified either by cesium chloride gradient centrifugation or by column chromatography on a Sepharose 4B column (Pharmacia, Uppsala, Sweden) as described in Maniatis et al., loc. cit. pp. 93-96. A recovery of about 400 μg DNA per liter culture is routinely obtained.

f) Vectors: dG-tailed pBR322 plasmid DNA (Bethesda Research Laboratories, Inc., Gaithersburg, MD) was used to clone the cDNA for t-PA and u-PA. The detailed molecular structure of pBR322 is described by Maniatis el al., loc. cit. pp. 5 and 488. The E. coli strains used for transformation with recombinant pBR322 were either HB101 or MM294 (Maniatis et al., loc. cit. p. 504).

All of the subcloning of DNA fragments from t-PA and u-PA genes were performed in pUC plasmids—a series of pBR322 derived vectors containing lac Z and ampicillinase genes (Vieria, J. and Messing, J., Gene 19, 259, 1982). In addition the plasmids also contain a sequence—multiple cloning or restriction site—in the lac Z, as shown below:

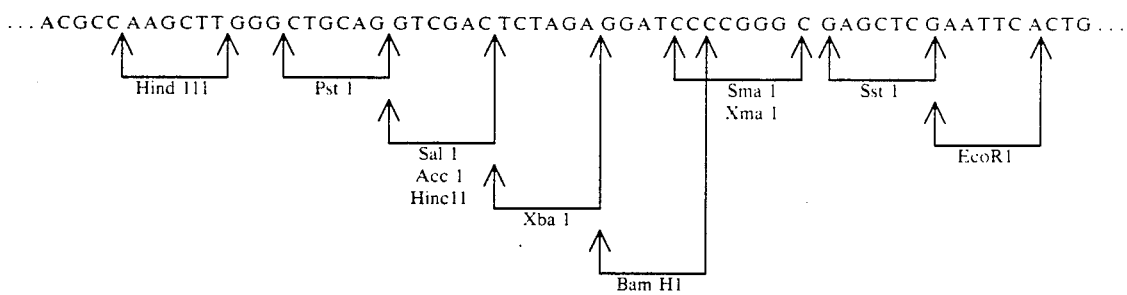

Cloning in any of the 11 sites can be monitored by the appearance of white recombinant colonies in the background of blue vector colonies on an indicator plate containing X-gal (5-bromo-4-Chloro-3-indolyl β-D-galactoside) (Ruther, Mol. Gen. Genetics 178, 475, 1980). The E. coli strain used for transformation with the recombinant pUC plasmid, was JM 103. The pUC plasmid and E. coli JM 103 were obtained from Pharmacia P-L Biochemicals, Milwaukee, WI.

g) Host/vector System
1. Microbial System

The work described here was performed using the microorganisms E. coli. K-12 strain JM 103 (PL Biochemicals) and E. coli K-12 strain MM294 (ATCC No. 33625). Other microorganisms which may be used in this process include other useful E. coli strains and Bacilli, such as Bacillus subtilis. All these microorganisms utilize plasmids that can replicate and express heterologous gene sequences.

The expression system in yeast employs a plasmid which is capable of selection and replication in *E. coli* and/or yeast (*Saccharomyces cerevisiae*). For selection in yeast, the plasmid contains the TRP 1 gene which renders a transformed trp-yeast strain (RH218) prototrophic for tryptophan. The yeast expression vector can shuttle in between yeast and *E. coli*. The plasmid has the following components: 1) a DNA segment derived from PBR 322 containing the origin of replication and the ampicillin resistance gene, 2) the yeast TRP 1 gene, 3) the yeast 2μ DNA which enables the plasmid to replicate in yeast with high stability, 4) A promoter region from the yeast gene, such as alcohol dehydrogenase, α factor, glyceraldehyde-3-phosphatedehydrogenase, etc., 5) translational start and transcriptional stop sequences which can be used for proper termination and polyadenylation of mRNA in the expression system.

2. Mammalian Cell Culture System

Mammalian cell lines capable of the replication and expression of a compatible vector for the production of heterologous proteins can be used in the present invention. They are, for example: Cos-7, W138, 3T3, CHO, Hela cells, and C127 cells. The vectors used contain 1) the origin of replication derived from a virus (SV40, adeno, polyoma, BPV) or cellular chromosomal DNA, 2) a promoter, 3) the translational initiation signals, such as ribosomal binding sites, and 4) RNA processing signals, (RNA splicing, polyadenylation and transcriptional terminator sequences). Specific examples of the expression vectors presented here use a BPV viral replication origin, a mouse metallothionein promoter and SV40 RNA processing signals. The vector can also be shuttled between mammalian cell culture and *E. coli*. It contains derivatives of PBR 322 sequences which provide selectable markers for *E. coli* ampicillin resistance as well as an *E. coli* origin of DNA replication. These sequences are derived from the plasmid pML-2d.

The edited hybrid plasminogen activator gene containing a Bam Hl sticky end is first inserted at the Bgl II site of plasmid 341-3 (Law MF et al., Md. Cell Biol. F 3,2110,1983) between the mouse metallothionein transcriptional promotor element and the SV40 early region transcriptional processing signals. The complete BPV genome, obtained after digestion of plasmid 142-6 (ATCC No.37134) with Bam Hl, is ligated to the unique Bam Hl site. Plasmid 341-3 also contains pML2, a pBR 322 derivative which allows plasmid replication in bacterial cells. The expression plasmid constructed herein can replicate in mouse C-127 cells exclusively as an extrachromosomal episome. Transfected cells can be selected for the transformed phenotype. Further modification of the expression vector, such as by adding specific enhancer elements for higher expression levels or inserting drug resistance (such as neomycin resistance) into the gene is also possible.

TRIS-KRINGLE PLASMINOGEN ACTIVATOR

Tissue Plasminogen Activator (t-PA)

Messenger RNA

Total RNA was isolated by the isothiocyanate method (Maniatis et al., loc. cit. p. 196) from normal human fibroblast cells (WI-38 cells), which had been stimulated by endothelial cell growth factor (ECGF) and heparin to produce t-PA. The same stimulated cells produce urokinase. Messenger RNA (mRNA) was obtained from the total RNA by chromatography on an oligo-deoxythymidine (dT)-cellulose column (Aviv et al., Proc. Nat'l. Acad. Sci. USA, 69, 1408, 1972). Further fractionation of the mRNA was performed by centrifugation in a 15–30% sucrose density gradient and individual mRNA fractions were hybridized with $^{32}$P-probes. (as described below). Fractions containing the t-PA message (ca. 20–24S) were pooled for use in the preparation of complementary DNA (cDNA).

Complementary DNA

The pooled mRNA (5 μg) described in the previous paragraph was used to produce double stranded cDNA and the cDNA was homopolymer tailed with polydeoxycytidylate (poly dC) using terminal nucleotide transferase. The product was annealed with Pst 1 digested, polydeoxyguanylate (poly dG) tailed pBR322. The annealed DNA was used to transform competent *E. coli* 294 cells which were cultured to produce about $10^5$ bacterial clones (Maniatis et al., loc cit., p. 229).

Screening and Identification of t-PA Clone

Figure 2:
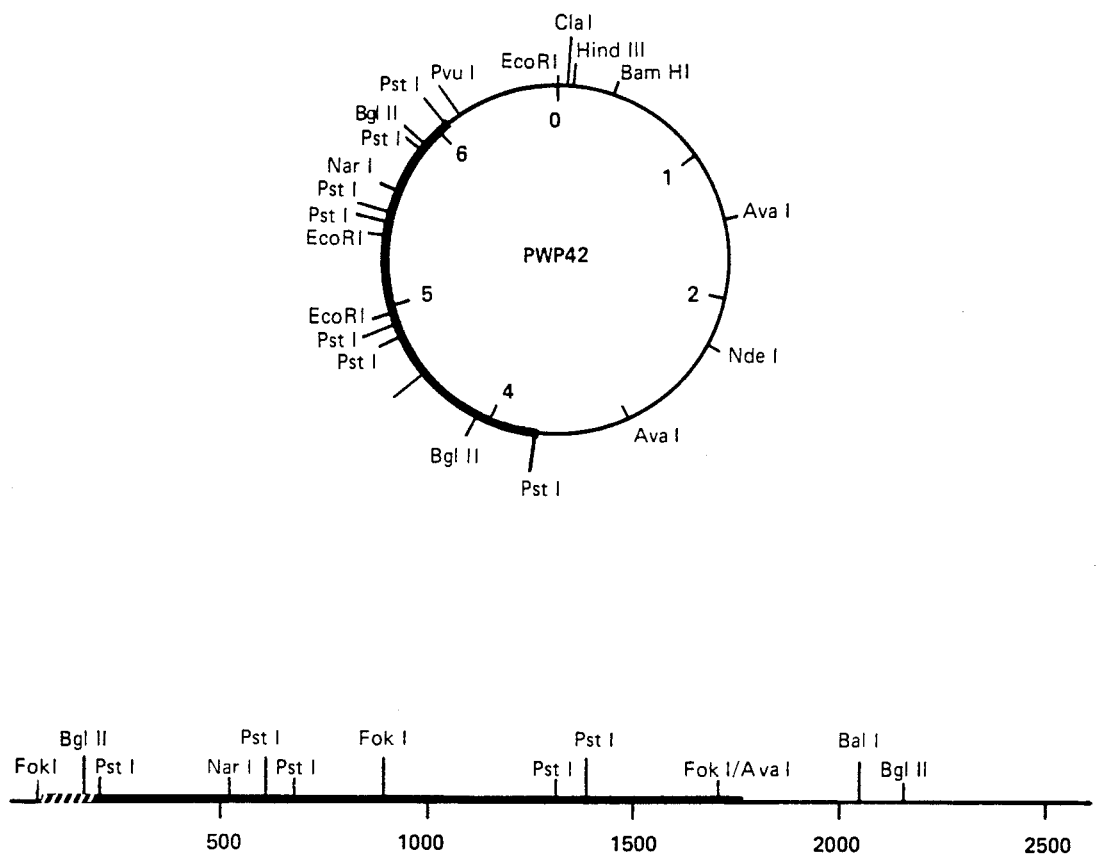
FIG. 2 depicts the restriction map of tissue plasminogen activator recombinant clone pWP-42.

The following three oligonucleotides, after radiolabeling with $^{32}$P-ATP, were used to screen the library of recombinant clones. These oligomers correspond to amino acid sequences, 34–39 (17 mer), 253–258 (18 mer) and 523–527 (15 mer) of t-PA molecule (Pennica, D. et al., Nature, 301 214, 1983) 17 mer: 5'-CCACTGTT-GCACCAGCA-3'; 18 mer: 5'-CACATCACAG-TACTCCCA-3'; 15 mer: 5'-CGGTCGCATGTT-GTO-3'. About 20 colonies exhibited moderate to strong homology with the pooled probes. Replating and rehybridization of these colonies gave 16 clones with positive signals. Plasmid DNA prepared from these clones was blotted on nitrocellulose paper and hybridized with individual probes. Two clones (42 and 62a) hybridized to both the middle (18 mer) and 3' end (15 mer) probes. Enzymatic digestion of plasmid DNA with Pst 1 showed that clone No. 42 contained the biggest insert of greater than 2 kilobase (Kb) in the form of three fragments of 1.1, 0.6 and 0.4 Kb. A complete restriction map of the clone (pWP 42) is depicted in FIG. 2 of the drawings. This clone contains the full length sequence for the t-PA gene, containing 2600 bp, which includes the 5'- and 3'-untranslated regions.

Editing of t-PA Gene

Approximately 10 μg of pWP 42 plasmid DNA was digested with 9 units Xho II at 37° C. for 2 hours. The reaction mixture was run on preparative 1.2% agarose gel and a 1618 bp DNA fragment was isolated by electrophoresis in agarose gel. After filling in cohesive ends with *E. coli* Polymerase 1 (Klenow fragment) and dNTPs (four deoxy nucleotide triphosphates- dATP, dGTP, dCTP and dTTP) 1 μg of the so modified DNA was ligated overnight with 300 ng of phosphorylated Sal 1 linker. After phenol/chloroform extraction and ethanol precipitation, the DNA was digested with 50 U of Sal 1 for four hours and the reaction mixture applied to a preparative 1% agarose gel to isolate the desired DNA fragment.

The DNA with Sal 1 ends was ligated to Sal 1 cut pUC 13 and used to transform *E. coli* JM 103 cells and the cells were plated out on ampicillin and X-gal plates. Eight ampicillin resistant, white colonies were selected and grown to prepare a mini-plasmid preparation. Two clones (ptPS34B and ptPS39) were found to contain the required DNA fragment. Ten μg of ptPS39 plasmid DNA digested to completion with Bam Hl and Nar 1 was run on preparative agarose gel to obtain a 1288 bp fragment coding for the C-terminal end of t-PA.

The 5' end of the t-PA gene was obtained by digestion of 10 μg of pWP 42 with four units of Hga 1 at 37° C. for eight hours. A 515 bp fragment was isolated by electrophoresis in 1% agarose gel. The cohesive ends of this DNA fragment were filled in with DNA polymerase 1 (Klenow fragment) and dNTPs and the product was ligated to Sma 1 cut pUC 13. After transforming E. coli JM 103 cells, approximately 75 ampicillin resistant, white colonies were obtained. Twenty four of these colonies were grown to prepare a miniplasmid preparation. The miniplasmid preparation was digested with Nar 1 and 17 clones were found to have the required insert in either orientation. One clone (pt PHga 4) was grown in 1.0 liter of LB medium containing ampicillin to obtain a large quantity of plasmid DNA using the boiling method. The plasmid DNA, pt PHga 4, was digested with Bam Hl and Nar 1 and electrophoresed on 1.2% agarose gel to isolate a 434 bp DNA fragment coding for the N-terminal end of t-PA.

Figure 3:
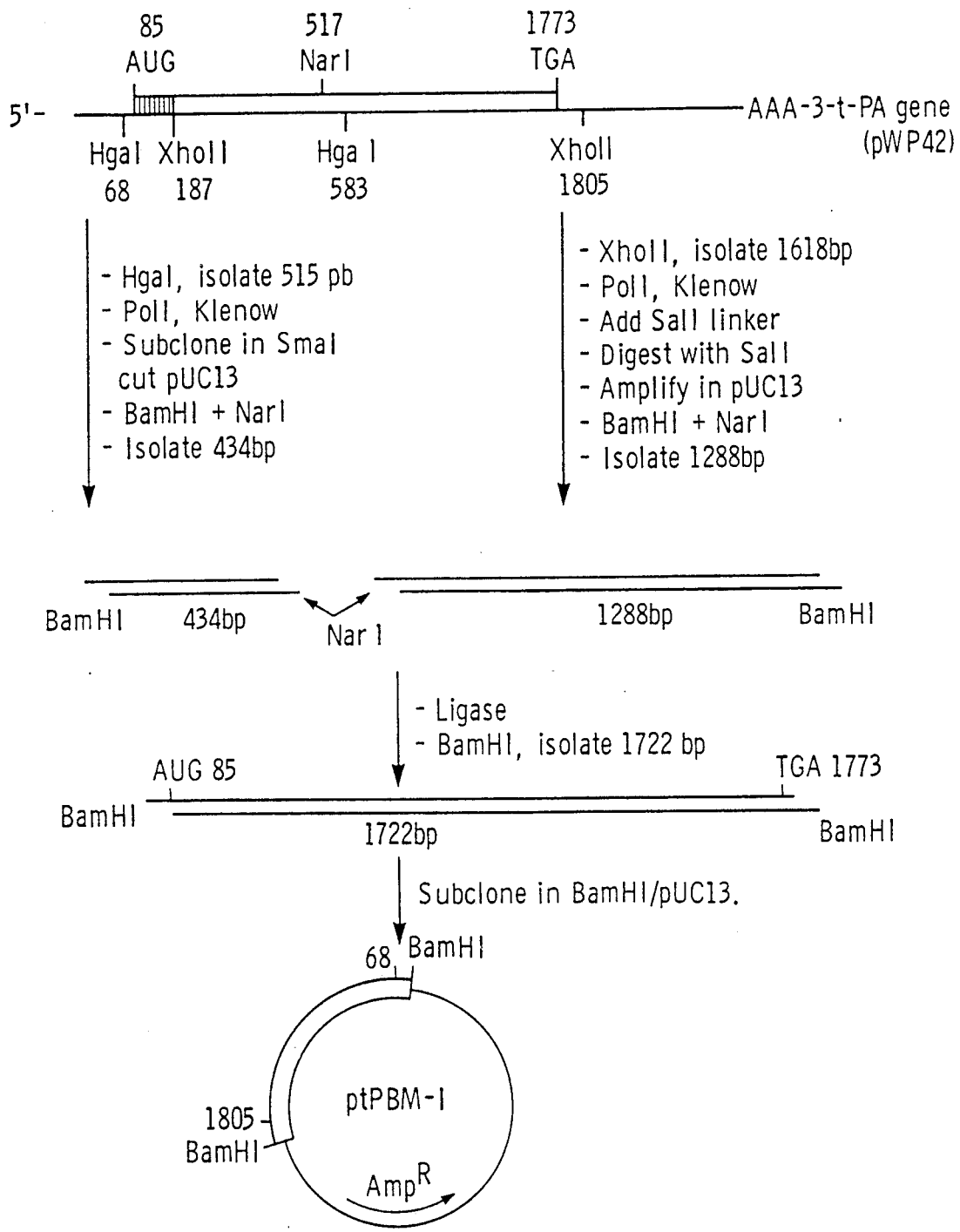
FIG. 3 presents the technique followed in production of plasmid ptPBM-1 from pWP-42. ptPBM-1 contains the genetic information needed to produce the complete t-PA molecule.
Figure 4:
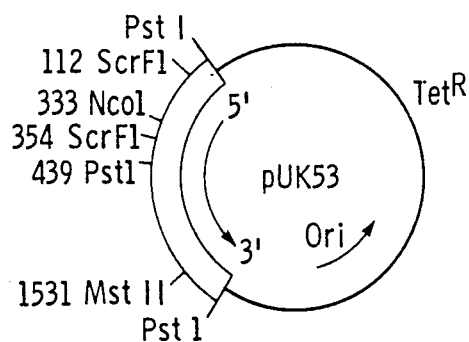
FIG. 4 presents the technique followed in production of plasmid pUKBM from plasmid pUK-53. pUKBM contains the genetic information needed to produce the complete urokinase protein.
Figure 4:
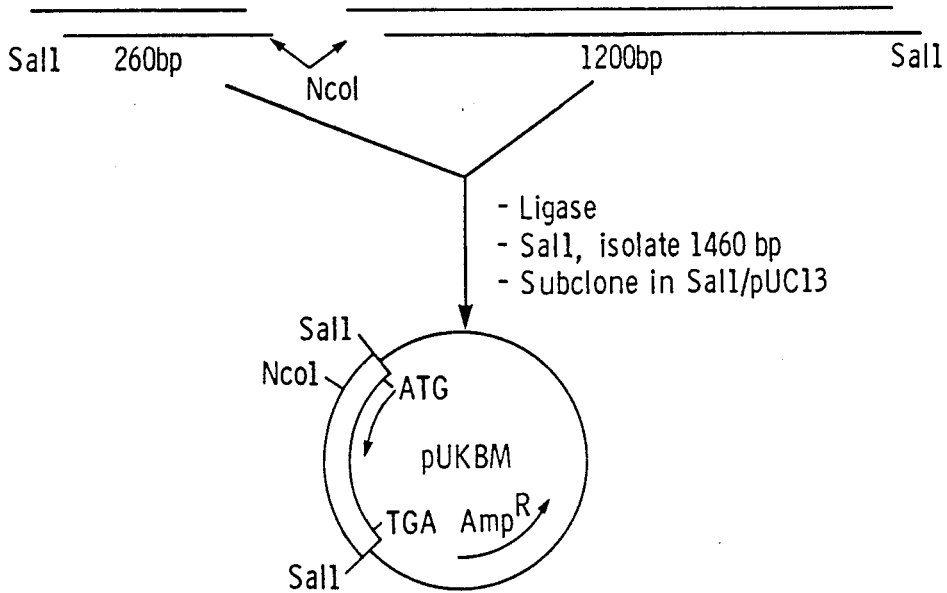

The 1288 bp DNA (300 ng) and 434 bp DNA (100 ng) were ligated overnight to obtain a 1722 bp DNA fragment. This DNA, after ligation with Bam Hl cut pUC 13 was used to transform E. coli JM 103 cells. More than 1000 ampicillin resistant colonies were obtained. Plasmid DNA from twelve colonies was prepared by the boiling method. The plasmid DNA was identified by cutting with each of Bam Hl, Nar 1 and Xho 11. All of the resulting plasmids were found to contain the desired 1,722 bp DNA fragment. One plasmid (pt PBM 1) was used for large scale plasmid DNA preparation. This plasmid, when cut with Bam Hl, gave rise to the 1,722 bp DNA coding for the complete t-PA molecule. The pt PBM 1 clone restriction map and a schematic diagram of its preparation is depicted in FIG. 3.

Urokinase Plasminogen Activator (u-PA)

Screening and Identification of u-PA Clone

The library of $10^5$ recombinant bacterial clones from which the t-PA gene was derived, supra, was screened with a radiolabelled 18 mer probe by the method of Grunstein et al., Proc. Nat'l. Acad. Sci. USA, 72, 3661, (1975). The probe, synthesized by the standard phosphotriester method using a Gene Machine (Applied Biosystems), presents the oligomer sequence -5'-GTA GAT GGC CGC AAA CCA-3'-corresponding to the middle part of the urokinase gene (aa$^{173-179}$). About 13 clones exhibited a moderate to strong hybridization signal. These clones were grown in 2 ml LB medium containing tetracycline and a miniplasmid preparation was prepared. The miniplasmid preparation was dissolved in 40 μL H$_2$O containing 10 μg/ml RNAse. About 8 μL of the DNA thereby produced was digested with one unit of Pst 1 and the product separated by electrophoresis on 1% agarose gel. One clone (pUK 53) was found to contain the largest insert of 1.7 Kb in the form of three inserts of sizes 1.2, 0.4 and 0.1 Kb long. The complete 3'-end nucleotide sequence of urokinase was present in the Pst 1 cut 1.2 Kb DNA fragment. The 5' end sequence of the gene was discovered, through nucleotide sequencing by the Maxam and Gilbert method, Methods Enzymol., 65, 1499, (1980) to be missing approximately 30 nucleotides corresponding to the first 10 amino acids of the signal peptide coding region of the urokinase protein. Therefore, a duplex DNA sequence corresponding to the missing nucleotides was synthesized and ligated to the existing gene.

Editing of Urokinase Gene

The urokinase plasmid (pUK 53) DNA is cut with Nco 1 and Mst II and the products separated by electrophoresis on 1% agarose gel. A DNA fragment of 1198 bp is isolated by electroelution. The 5' protruding end of the DNA fragment corresponding to the Nco 1 cut is made blunt ended by filling in with dNTP's and E. coli DNA polymerase (Klenow fragment). The DNA is then ligated to Sma 1 cut pUC 13 and the modified plasmid is used to transform competent E. coli JM 103 cells. The Nco 1 site of the insert is regenerated when the DNA is ligated to the Sma 1 site of pUC 13. The cells are plated out on ampicillin and X-gal plates and a miniplasmid preparation is produced from white colonies. Digestion of the miniplasmid DNA preparation with Nco 1 and Sal 1 gives an approximate 1200 bp DNA fragment. A large scale plasmid DNA preparation from a positive clone (pUKNM-3') is made and digested with Nco 1 and Sal 1 to obtain a large amount of the approximate 1200 bp DNA fragment which is separated by preparative agarose gel electrophoresis.

To provide the approximate 30 nucleotides corresponding to the first 10 amino acids of the 5' signal peptide coding region of the urokinase protein, pUK 53 plasmid DNA is digested first with Pst 1 and a 400 bp DNA fragment was isolated. This DNA was then treated with ScrFl to yield a 242 bp fragment of DNA. The protruding ends of the DNA are filled in with dNTP's and E. coli DNA polymerase 1 (Klenow fragment).

Two complementary oligonucleotide sequences, 38 and 42 bases in length, were synthesized on a Gene Machine to provide for missing amino aids ($-9$ to $-20$) while keeping the proper translational reading frame and providing a Sal 1 sequence on both ends of the DNA for subcloning in Sal 1 cut pUC 13. The two oligomers are mixed in equimolar amounts in ligase buffer (50 mM Tris.HCl, ph 7.6, 10 mM MgCl$_2$, 10 mM dithiothreitol) and heated to 80° C. for 5 minutes and allowed to cool to room temperature for about 1 hour. The thus formed duplex of the two complementary nucleotide sequences (about 1 μg) is ligated to about 300 ng of the 242 bp DNA fragment in ligase buffer at 4° C. for 16 hours using 400 units of T4 DNA ligase. The ligated mixture is separated by electrophoresis on 1.2% agarose gel and an approximate 320 bp DNA fragment is isolated by electroelution. This fragment (about 20 ng) is ligated to 100 ng. of Sal 1 cut pUC 13 and the vector is used to transform competent E. coil JM 103 cells. The cells were plated out on ampicillin X-gal plates. Twelve white colonies were selected and grown to prepare a miniplasmid preparation. The miniplasmid preparation is cut with Sal 1. One clone, containing the expected 320 bp DNA insert, is grown for large scale preparation of plasmid DNA. The DNA is cut with Sal 1 and Nco 1 to yield a 260 bp DNA fragment upon preparative agarose gel electrophoresis.

The 260 bp DNA and 1200 bp DNA fragments, containing a common Nco 1 restriction site at 333 bp position of the gene, are mixed in equimolar amounts for ligation. The ligated product is cut with Sal 1 and the reaction mixture separated by preparative 1% agarose gel electrophoresis. A 1460 bp DNA fragment is isolated by electroelution. This DNA is ligated to Sal 1 cut pUC 13 and this plasmid is used to transform competent

*E. coli* JM 103 cells which are plated out on ampicillin and X-gal plates. Twelve white colonies were selected and grown to prepare a miniplasmid preparation by the boiling method. The miniplasmid preparation is cut with Sal 1 and one clone (pUKBM) was found to contain the desired 1460 bp DNA insert. pUKBM was grown in large volume to provide plasmid DNA. The oligonucleotide sequence from the 5' end containing the synthetic linker was sequenced by the Maxam-Gilbert method to confirm its authenticity.

The DNA insert in pUKBM plasmid was thereby established to contain the translational initiation codon AUG (met, −20 aa in the leader sequence) as well as the termination codon TGA. This complete gene codes for the 20 amino acids of the signal peptide (−1 to −20) and the 411 amino acids of mature urokinase protein.

EXAMPLE 1

(UKaa$^{1-131}$-Ser-Glu-Gly-Asn-Ser-Asp)$^{1-91}$t-PA

In compound (a.) shown in FIG. 1, the t-PA sequence containing the signal peptide (a.a. −35 to −1) and the N-terminal peptide (a.a. 1 to 91) regions are replaced by an amino acid sequence containing the signal peptide (a.a. −20 to −1) and the first 131 amino acids of urokinase. The u-PA sequence is joined to the first kringle (tPK1) of t-PA via a oligonucleotide sequence coding for the hexapeptide L-Ser-L-Glu-Gly-L-Asn-L-Ser-L-Asp.

About 10 μg of plasmid pUKBM is digested with Eco R1 and Mst 1 under standard conditions. The reaction mixture is electrophoresed through a 1.2% agarose gel at 150 volts for 3 hours. After staining the gel with ethidium bromide to visualize the DNA bands, a 452 bp DNA fragment is isolated and purified. This DNA fragment contains coding information for the leader or signal peptide (20 amino acids) as well as N-terminal and kringle region (a.a. 1 to 131) of the urokinase gene.

In order to obtain the t-PA-des a.a 1-91 sequence, about 10 μg of recombinant plasmid ptPBM-1 is digested to completion with Ava II and electrophoresed on a 1.2% agarose gel to isolate a 747 bp DNA fragment. The addition of an oligomer linker to this fragment followed by digestion with Eco R1 to obtain a 354 bp DNA fragment is described in Example 2 and depicted in FIG. 7. The 354 bp DNA codes for the hexapeptide linker and the t-PA peptide (a.a. 92 to 204)—a 118 amino acid sequence. Equimolar amounts of the 452 bp DNA fragment prepared in the preceding paragraph and the 354 bp DNA fragment were ligated using T4 DNA ligase at 15° C. for 16 hours. The reaction mixture is separated by electrophoresis on 1.2% agarose gel and a DNA band corresponding to a size of 806 bp was eluted out and purified. About 100 ng of 806 bp DNA fragment was ligated with about 300 ng of BAP (bacterial alkaline phosphatase) treated Eco R1 pUC 13 (Pharmacia P-L Biochemicals, Inc. Milwaukee, WI) in about 20 μl reaction volume. About ¼ of the solution was used to transform competent *E. coli* JM 103 cells according to the procedure of Viera, J. and Messing, J., Gene 19, 259, (1982). Miniplasmid DNA prepared from 12 recombinant white colonies, was digested with Eco R1 under standard conditions. One clone, ptPUK-806, containing the required insert, was digested with Bam H1 and Nar 1 and separated by electrophoresis on 1.2% agarose gel. A DNA band corresponding to a 519 bp fragment was cut, eluted and purified. Following the same procedure, a 1300 bp DNA fragment was obtained by digestion of ptPBM-1 with Bam H1 and Nar 1. Equimolar amounts of 519 bp and 1300 bp DNA fragments were used for ligation following the standard procedure of Goodman, H. M., and MacDonald, R. J., Method. Enzymol 68, 75, (1979). The ligation mixture was extracted twice with a phenol:chloroform (1:1) mixture and the DNA was precipitated with two volumes of absolute ethanol. After dissolving the pellet in 50 μl H$_2$O, the DNA was digested with Bam H1 under standard assay conditions and separated by electrophoresis on a 1% agarose gel. A DNA fragment containing 1819 bps, was cut, eluted from the gel and purified. This DNA fragment contains all the coding information required for the signal peptide (20 amino acids) and the mature hybrid or triskringle PA molecule of 573 amino acids which corresponds to (UKaa$^{1-131}$-Ser-Glu-Gly-Asn-Ser-Asp)$^{1-91}$-t-PA depicted in FIG. 1(a).

The tris-kringle gene is then ligated to Bgl II cut expression vectors bovine papilloma virus (BPV) which serves as the complete expression vector. Conventional culture yields the tris-kringle plasminogen activator of FIG. 1(a).

Construction of Urokinase Kringle Sequence

Figure 6:
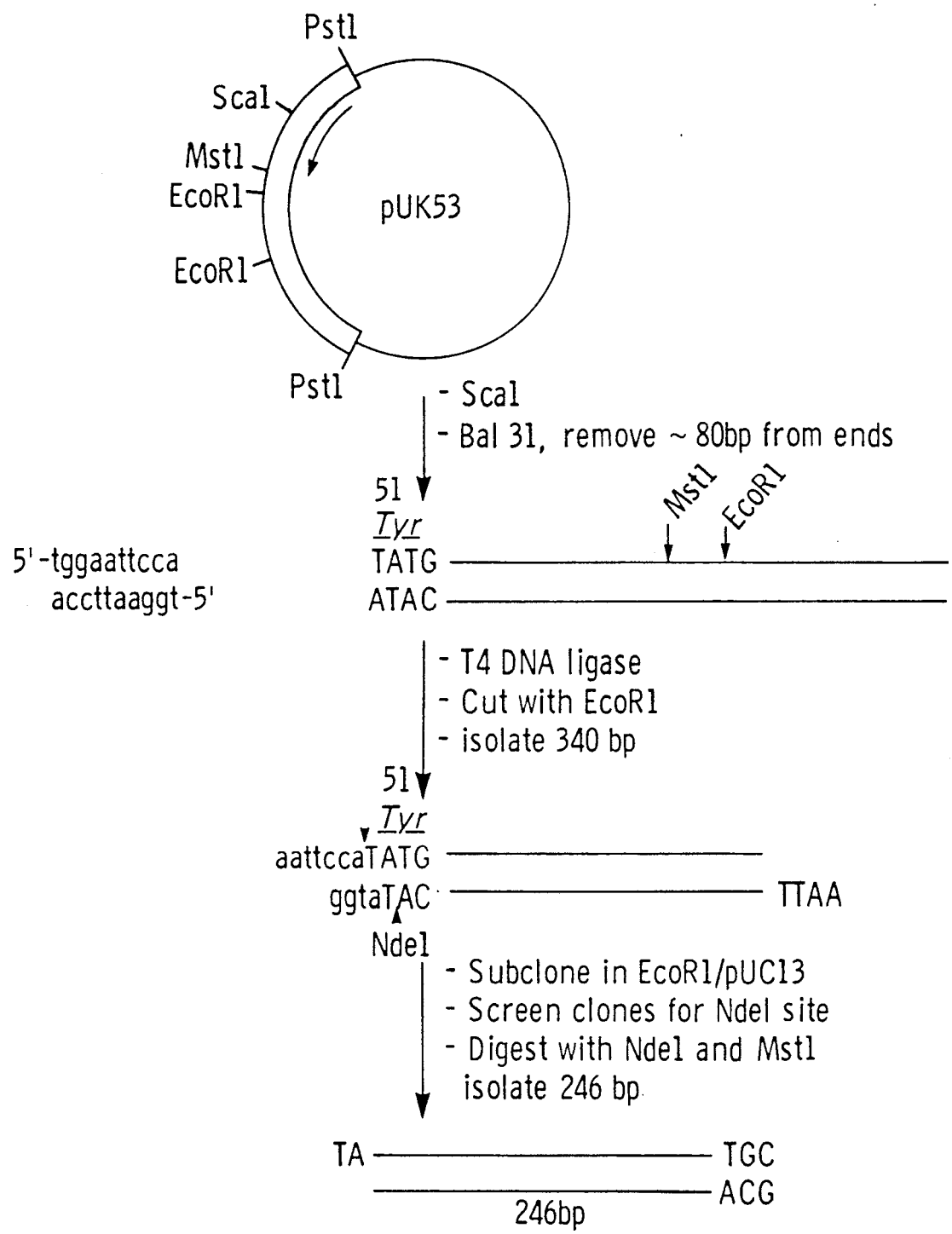
FIG. 6 presents a flow diagram of the method followed to produce the gene coding for amino acids 51-131 of urokinase (u-PA$^{51-131}$).

In Examples 2 and 3, only the kringle part (a.a. 50-131) of urokinase is utilized and is inserted either before or after the double kringle region of t-PA. FIG. 6 depicts the construction of a nucleotide sequence, coding for a.a. 51-131 from the recombinant plasmid pUK 53. There is a convenient restriction site, Mst 1, just after the nucleotide sequence corresponding to amino acid 131. However, none could be found around a.a. 50. Thus, a scheme for the creation of a restriction site around a.a. 50 (Nde 1 in this example) was formulated as shown in FIG. 6. The kringle region of urokinase corresponds to the nucleotide sequence from bp 284 (a.a 50) to bp 530 (a.a. 131).

Figure 7:
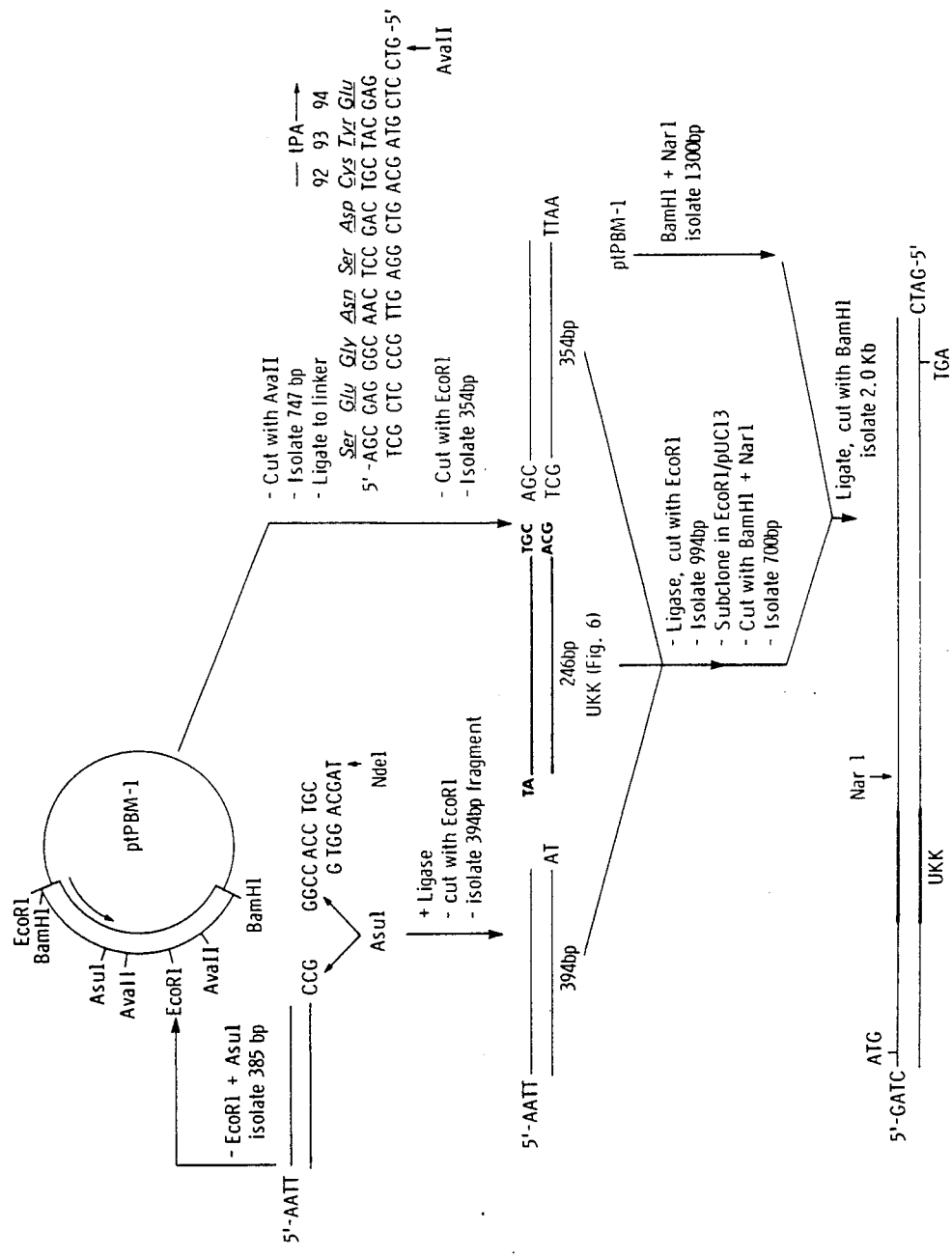
FIG. 7 presents a flow diagram of the method followed to produce the gene coding for the tris-kringle product depicted in FIG. 1(b).
Figure 8:
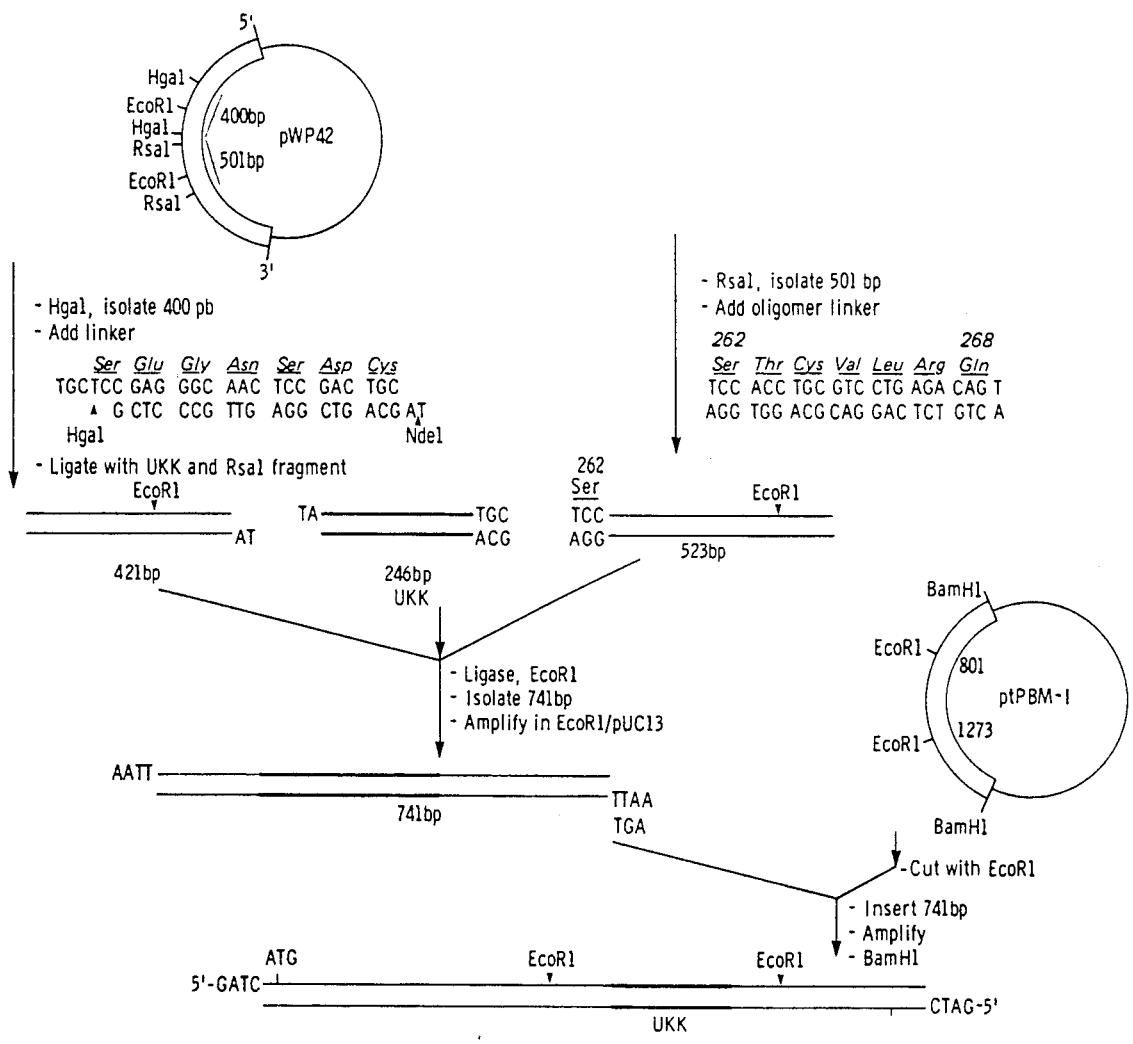
FIG. 8 presents a flow diagram of the method followed to produce the gene coding for the tris-kringle product depicted in FIG. 1(c).

About 10 μg of pUK 53 plasmid DNA was digested to completion with Sca 1 which cuts at bp 204 in the urokinase sequence. After phenol extraction and ethanol precipitation, the DNA pellet was dissolved in 50 μl of buffer solution (10 mM CaCl$_2$, 12 mM MgCl$_2$, 0.2M NaCl 1, 20 mM Tris.HCl (pH 8.0), 1 mM EDTA). To the reaction mixture was added 1 μl (2 units) of nuclease Bal 31 and the mixture was incubated at 30° C. for 15 seconds (Legerski, R. J., J. L. Hodnett, and H. B. Gray, Jr., Nucleic Acid Res. 5, 145, 1978). The reaction was stopped by the addition of 5 μl of 0.4M EGTA. This reaction time was found to be sufficient to remove about 80 bp from each end of the DNA fragment. After phenol extraction and ethanol precipitation, the DNA was ligated to an oligonucleotide linker (10 bp) under standard reaction conditions. The oligomer linker (Eco R1/Nde 1 linker) with the sequence, TGGAATTCCA, was designed to create an Nde 1 site (CATATG) when ligated to the DNA fragment end containing the sequence, TATG (corresponding to a.a. 51). In addition, the restriction site, Eco R1, was built into the linker to provide for subsequent cloning in a pUC 13 vector. After phenol extraction and ethanol precipitation, the DNA was digested with Eco R1 and separated by electrophoresis on 1% preparative agarose gel. A DNA band corresponding to 340 bp, was cut, eluted and ethanol precipitated. About 40 ng of this DNA was ligated with about 0.4 μg of Eco R1 cut pUC 13 vector DNA and used to transform competent *E. coli* JM 103 cells (Maniatis et al., loc. cit. p. 250). About 1,000 recombinant colonies were obtained from 10 plates. The bacterial colonies were replica-plated on nitro-cellulose paper, and screened by in situ hybridization using a radioactive oligonucleotide probe (Grunstein et al. Proc. Nat'l. Acad. Sci USA 72, 3961, 1975). The oligonucleotide probe used was 18 bp long (TTCCATATGAGG-GGAATG) and contains the first five nucleotides from the Eco Rl /Nde 1 linker and the next 13 bases from the urokinase sequence corresponding to a.a 51 to 54. About 12 clones showed a moderate to strong signal on X-ray film. Miniplasmid DNA prepared from these 12 clones was digested with Nde 1 and separated by electrophoresis on 1% agarose gel. One clone, pUKKNd 16, was found to contain the newly generated Nde 1 site. This plasmid DNA, after digestion with Nde 1 and Mst 1, was separated by electrophoresis on 1.4% agarose gel to obtain a 246 bp DNA fragment. This DNA fragment contains the urokinase nucleotide sequence coding for a.a. 51 to 131. The DNA sequence for the missing a.a. 50 (Cys) is incorporated into the oligomer linker as shown in FIG. 7 and 8.

EXAMPLE 2

91-(UKaa$^{50-131}$-Ser-Glu-Gly-Asn-Ser-Asp)-92-t-PA

The urokinase kringle sequence as shown in FIG. 1(b) was inserted before the double kringle region of t-PA i.e. between a.a. 91 and 92. As described in the preceding paragraph, Nde 1 and Mst 1 digestion of pUKKNd 16 plasmid DNA gave rise to a 246 bp sequence which corresponds to a.a. 51 to 131 of urokinase. The two ends of the UK kringle sequence (246 bp) were inserted into the t-PA gene between nucleotide no. 462 (a.a. 91) and 463 (a.a. 92) through the use of two oligonucleotide linkers. The procedure followed is shown in FIG. 7.

About 50 μp of ptPBM-1 plasmid DNA was digested with Eco Rl and a 740 bp DNA fragment was isolated by electrophoresis in 1% agarose gel. This DNA was then digested partially with Sau 961 (isoschizomer of Asu 1) for the isolation and purification of a 385 bp DNA fragment.

Two complementary oligonucleotide sequences were synthesized by the phosphotriester method (Crea et al., Proc. Nat'l. Acad. Sci (USA) 75, 5765, 1978) which code for amino acid 91 (Thr) of t-PA and amino acid 50 (Cys) of the urokinase kringle.

```
              Thr   Cys
   5'-GGCC    ACC   TGC
           G  TGG   ACGAT-5'
         Asu 1      Nde 1
```

The oligonucleotide linker is flanked by Asu 1 and Nde 1 restriction sites. Only the upper oligonucleotide (GGCCACCTGC) was phosphorylated at its 5' end.

About 1 μg of the 385 bp DNA fragment was ligated overnight with approximately 1 μg of oligomer linker. After phenol extraction and ethanol precipitation, the DNA was digested for 2 hours with Eco Rl and separated by electrophoresis on 1.2% agarose gel to obtain a 394 bp DNA fragment. This DNA fragment contains the nucleotide sequences coding for the signal peptide (35 a.a.) and N-terminal peptide a.a. 1-91 of t-PA. In addition, it also restores the DNA sequence for a.a. 50 (Cys) of the UK kringle not present in its 246 bp DNA fragment (FIG. 6).

In order to obtain the C-terminal t-PA sequence, amino acids 92 onward, about 50 μg of ptPBM-1 plasmid DNA was digested with Ava II and a 747 bp DNA fragment was isolated from 1% agarose gel. Two complementary DNA fragments of 27 and 30 bp long were synthesized by the phosphotriester method. As shown in FIG. 7, this DNA linker codes for the hexapeptide Ser-Glu-Gly-Asn-Ser-Asp and also restores the missing a.a. 92 to 94 (Cys-Tyr-Glu) in the Ava II cut 747 bp DNA. Only the lower oligomer (30 ) is phosphorylated at its 5' end. About 1 μg of 747 bp DNA and 1 μg of oligomer linker were ligated overnight at 15° C. After phenol extraction and ethanol precipitation, the DNA was digested for 2 hours with Eco Rl to obtain a 354 bp DNA fragment from 1.4% agarose gel. About 500 ng of each of the three DNA fragments, 394 bp, 246 bp (UK Kringle) and 354 bp, were ligated overnight using T4 DNA ligase. After phenol extraction and ethanol precipitation, the DNA was digester with Eco Rl and a 994 bp DNA fragment was isolated and purified from the 1% agarose gel. This DNA, after ligation with an equimolar amount of Eco Rl cut pUC 13 vector, was used to transform competent E. coli JM 103 cells. Miniplasmid DNA preparations from 12 recombinant clones were digested with Eco Rl. One clone containing the required insert of 994 bp, was grown in 1 liter LB medium for large scale preparation of plasmid DNA. About 10 μg of this plasmid DNA was digested with Bam Hl and Nar 1 and a DNA fragment corresponding to 700 bp size was purified from the 1% agarose gel.

The 3' end of the t-PA gene was obtained by digestion of about 10 μg of ptPBM-1 plasmid DNA with Bam Hl and Nar 1. After separating the reaction mixture by electrophoresis on 1% agarose gel, an approximate 1300 bp DNA fragment was isolated by electroelution and purified.

Approximately equimolar amounts of the two DNA fragments of 700 bp and 1300 bp size, were ligated overnight and a 2000 bp DNA fragment was recovered from 1% agarose gel. This DNA, flanked by the restriction enzyme Bam Hl sequence, is inserted at the Bgl II site of the BPV expression vector. This DNA codes for a protein containing a total of 650 amino acids—35 amino acids for the signal peptide and 615 amino acids for the mature protein. Conventional culture, recovery, isolation and purification techniques yield the tris-kringle plasminogen activator of FIG. 1(b).

EXAMPLE 3

261-(Ser-Glu-Gly-Asn-Ser-Asp-UKaa$^{50-131}$)-262-t-PA

In this example, the urokinase kringle sequence is inserted just after the double kringle region of the t-PA gene i.e. between the sequences corresponding to a.a. 261 (Cys.) and 262 (Ser). FIG. 8 shows the scheme detailing the various steps involved in the production of this tris-kringle PA.

About 10 μg of pWP 42 plasmid DNA was digested with Hga 1 and a 400 bp DNA fragment was isolated from 1% agarose gel. This DNA fragment contains the sequence corresponding to part of the kringle region of t-PA, i.e., amino acids 135-261. It should be noted that the double kringle region of t-PA ranges from amino acids 92 to 261, with a hexapeptide (amino acids 174-179) joining the two kringles. An oligonucleotide linker consisting of two DNA sequences—24 mer and 21 mer as depicted in FIG. 8—was synthesized using the phosphotriester method. This oligomer linker codes for the hexapeptide linker as well as for missing amino acid 50 (Cys) of the UK kringle and is flanked by restriction enzyme sequences for Hga 1 and Nde 1. Only the upper oligonucleotide, 23 mer is phosphorylated at its 5' end and it is ligated to the Hga 1 end of the 400 bp DNA fragment from t-PA. The 421 bp DNA product is isolated from preparative 1% agarose gel.

The post kringle part of t-PA was obtained by digestion of 10 μg of pWP 42 plasmid DNA with Rsa 1 followed by isolation of 501 bp DNA from 1.2% agarose gel. This DNA represents a.a. 269 to 435 of the t-PA molecule. Two complementary oligonuclelotide sequences of 22 bases as depicted in FIG. 8 were synthesized by the phosphotriester method. This DNA linker, when ligated to the 501 bp DNA at its 5' end restores the missing amino acids from 262 to 268.

Approximately 1 μg of the 501 bp DNA and 1 μg of the linker DNA were ligated overnight and a DNA band corresponding to 523 bp size was purified from 1% agarose gel.

The three DNA fragments of sizes 421 bp, 246 bp (UK Kringle) and 523 bp, were ligated in approximately equimolar amounts at 15° C. for 16 hours. After phenol extraction and ethanol precipitation, the DNA was cut with Eco Rl and a DNA fragment of 741 bp was isolated. This DNA, flanked by two Eco Rl restriction sites, was amplified in pUC 13 vector system as described above.

10 μg of ptPBM-1 plasmid DNA in which the Eco Rl site in multiple cloning site had been removed, was digested to completion with Eco Rl and the larger vector DNA fragment of about 4.0 Kb was isolated from 1% agarose gel. About equimolar amounts of Eco Rl cut vector DNA and the 741 bp DNA were ligated and the product used to transform competent *E. coli* JM 103 cells. Miniplasmid DNA, prepared from 12 recombinant clones, was digested with Bam Hl to look for the desired insert of about 1.8 Kb. The correct orientation of the 741 bp DNA in the insert was determined by digestion of the plasmid DNA with Nar 1 and Mst 1. One clone, ptPUHYC, when digested with Nar 1 and Mst 1 was found to contain a fragment of approximately 700 bp in correct orientation.

The 1.8 Kb DNA, obtained by digestion of ptPUHYC plasmid DNA with Bam Hl, contains the nucleotide sequence coding for a protein of 650 amino acids-35 amino acids for the signal peptide and 615 amino acids for mature protein corresponding to the product of FIG. 1(c).

The tris-kringle gene is then ligated to Bgl II cut bovine papalloma virus (BPV) which serves as the complete expression vector. Conventional culture yields the tris-kringle plasminogen activator of FIG. 1(c).

TETRA-KRINGLE PLASMINOGEN ACTIVATOR

Prothrombin cDNA

A cDNA clone for the prothrombin gene was isolated from the human liver cDNA library following the procedure of Friezner et. al., Biochemistry, 22, 2087, 1983. The clone, pPTR, contains complete coding information for the mature protein of 579 amino acids. The double kringle region of prothrombin extends from amino acid 65 (bp 319) to amino acid 248 (bp 840), a 184 amino acid peptide. Each of the two kringles, PTK1 (amino acids 65-143) and PTK 2 (amino acids 170-248) are 79 amino acids long and are joined by a peptide of 26 amino acid length (amino acids 144-169).

Preparation of Prothrombin Double Kringle Sequence

Figure 12:
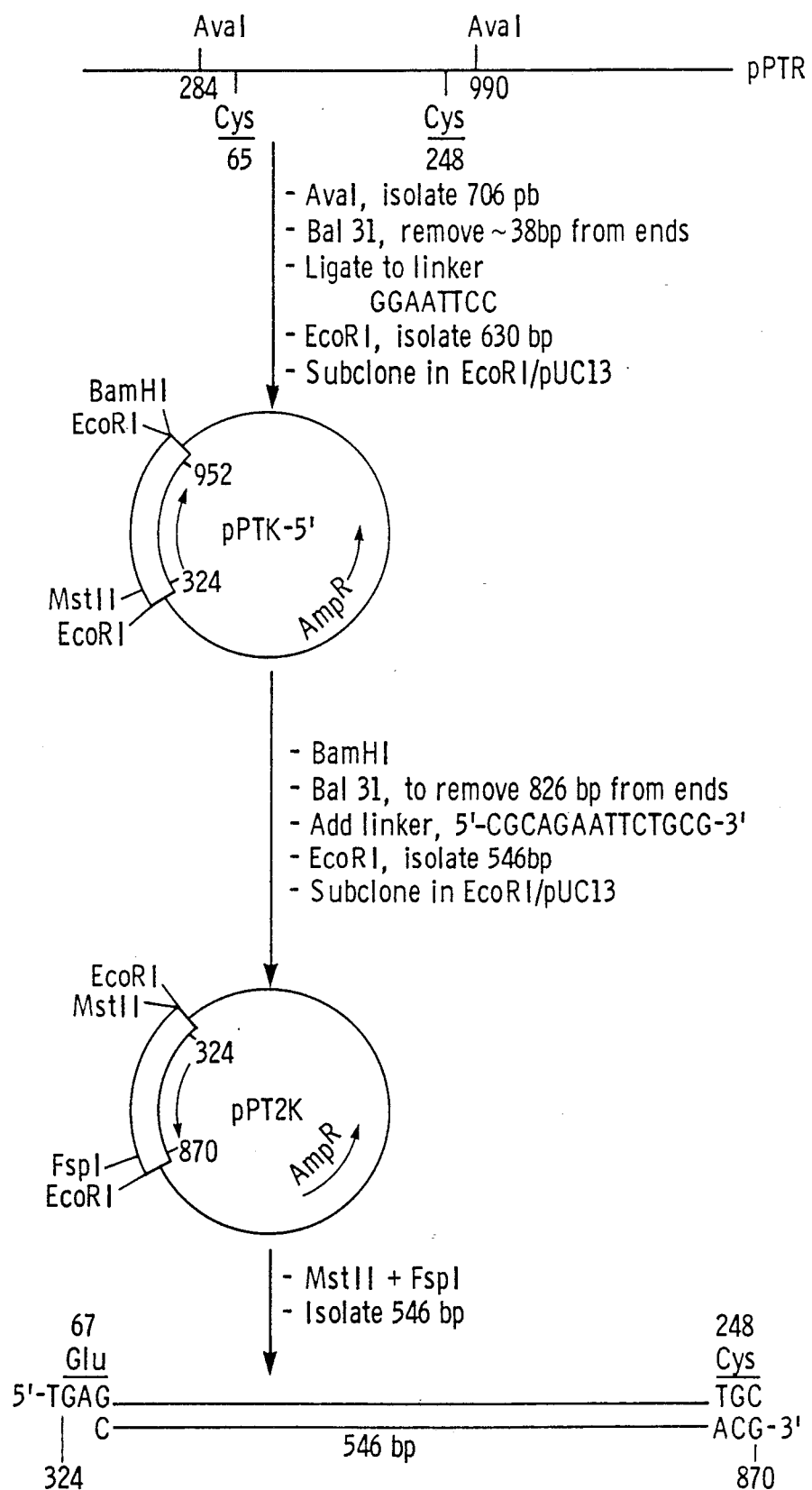
FIG. 12 presents a flow diagram of the method followed to produce the gene coding for the double kringle region of prothrombin.

The DNA sequence representing the double kringle region was isolated from the prothrombin cDNA in two steps (FIG. 12).

In the first step, 10 μg of pPTR plasmid DNA was digested with Ava 1 and a 706 bp DNA was isolated from 1% agarose gel. This DNA was treated with Bal 31 for 7.5 seconds to remove about 38 bp from either end of the DNA (Legerski et. al., Nucleic Acid Res., 5, 145, 1978). After phenol extraction and ethanol precipitation, the DNA was ligated to an Eco Rl linker, GGAATTCC, at 4° C. for 15 hours. This linker, when ligated to DNA ending with sequences CTGAG or TGAG (amino acid 67, Glu) will produce a new restriction sequence for Mst II (CCTGAGG) at the N-terminal of the double kringle (amino acid 67). After cutting with Eco Rl, a DNA fragment of 630 bp size was isolated. This DNA, after ligation in equimolar amounts with Eco Rl/pUC 13, was then used to transform competent *E. coli* JM 103 cells. Initial screening for the desired clone was performed by in situ hybridization with a $^{32}P$ labeled probe, GAATTCCT-GAGGGTCTG, containing nucleotide sequences for amino acids 66 to 68. Twelve clones, exhibiting a strong signal on X-ray film, were grown for a miniplasmid preparation. After digestion of plasmid DNA with Mst II and Bam Hl, one clone, pPTK-5' was found to contain the required insert of about 630 bp and also the newly created Mst II site at 322 bp.

Figure 13:
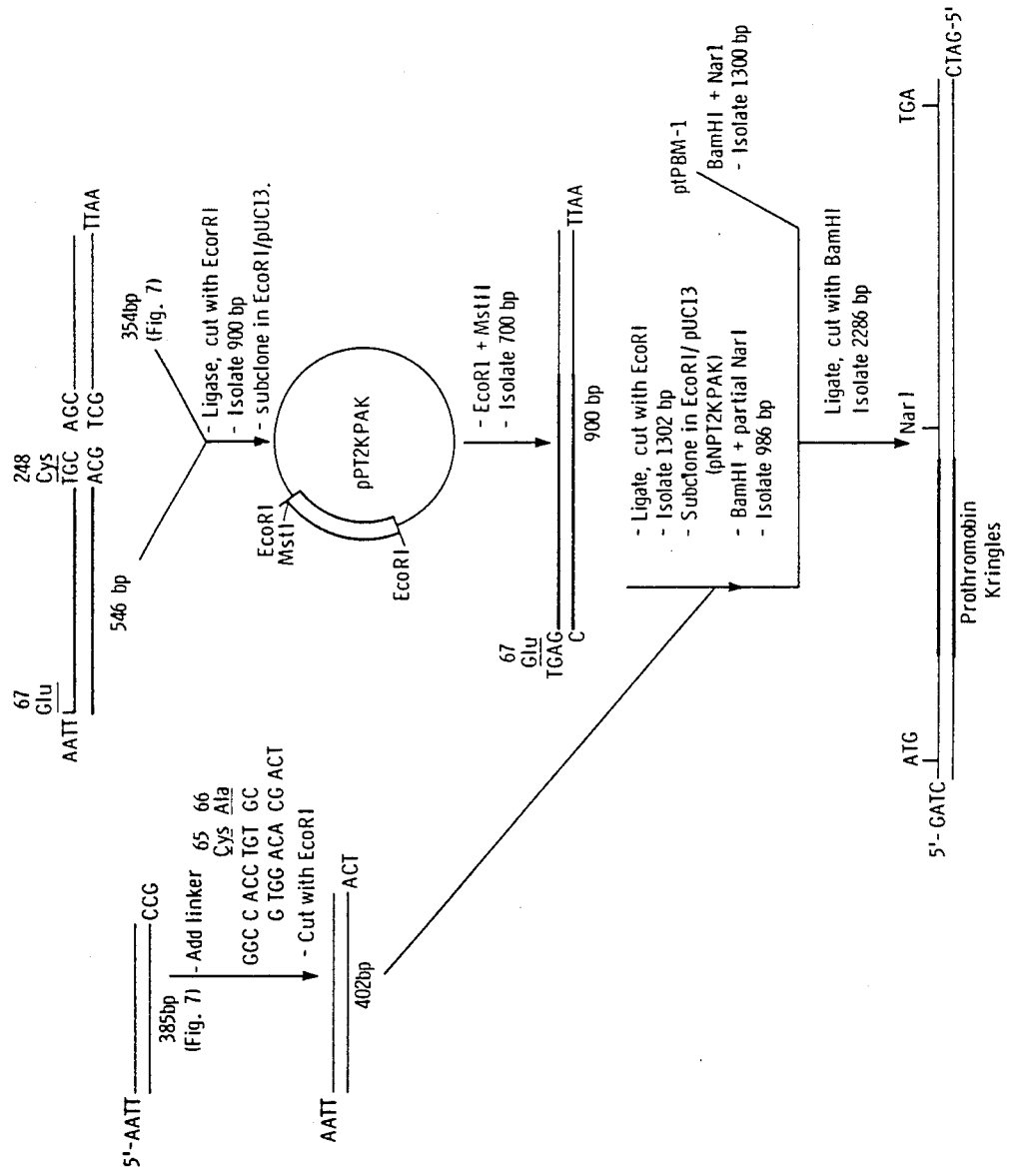
FIG. 13 presents a flow diagram of the method followed in producing the gene coding for the tetra-kringle product depicted in FIG. 1(d).

The second step involved the editing of the 3' end of the kringle region, around amino acid 248, using a similar approach as described above. About 10 μg of pPTK-5' plasmid DNA was digested to completion with Bam Hl. The DNA was then treated with Bal 31 for 15 seconds at 30° C. to remove about 82 bp from both ends of the DNA. After phenol extraction and ethanol precipitation, the DNA was ligated to a Eco Rl/Fsp 1 linker, CGCAGAATTCTGCG. As the name suggests, the linker generates an Fsp I sequence (TGCGCA) at any DNA sequence ending in TG-. After cutting thoroughly with Eco Rl, a 546 bp DNA was isolated from 1.2% agarose gel and then ligated to Eco Rl cut pUC 13. The recombinant plasmid was then used to transform competent *E. coli* JM 103 cells. About 1000 recombinant clones were screened in situ using a $^{32}P$-labelled oligomer with the sequence CTCAACTATTGCGCAGAA (amino acids 245 to 248). Plasmid DNA prepared from 12 potential clones, was cut with Mst II and Fsp 1 and run on a 1% agarose gel. One clone, pPT2K, was found to contain the required insert of 546 bp size. This DNA codes for a total of 182 amino acids, amino acids 67–248, of the double kringle region. The nucleotide sequence for the remaining two amino acids, at positions 65 (Cys) and 66 (Ala), are added via the oligomer linker as shown in FIG. 13.

EXAMPLE 4

91(PTKaa$^{65-248}$-Ser-Glu-Gly-Asn-Ser-Asp)-92-t-PA

The double kringle sequence of prothrombin, amino acids 65–248, was inserted before the double kringle region of t-PA (i.e. between amino acids 91 and 92) to give rise to tetra kringle-PA. As described in the preceding paragraph, Mst II+FspI or Eco Rl digestion of pPT2K plasmid DNA gives rise to a 546 bp DNA fragment which codes for amino acids 67 to 248 of prothrombin. Through the use of two oligonucleotide linkers, the two ends of the 546 bp DNA were inserted into the t-PA gene between nucleotide 462 (amino acid 91) and 463 (amino acid 92). The scheme followed is shown in FIG. 13.

The 354 bp DNA, containing the nucleotide sequence for the peptide linker Ser-Glu-Gly-Asn-Ser-Asp as well as for the amino acid 92 to 204 of t-PA, was prepared as described in Example 2 and FIG. 7. Equimolar amounts of the 354 bp DNA and 546 bp DNA (prothrombin kringles) was ligated at 4° C. for 16 hours. The DNA was cut with Eco Rl and a 900 bp DNA fragment was isolated from agarose gel. This DNA after ligation to Eco Rl cut pUK 13 vector was used to transform *E. coli* JM 103 cells. Miniplasmid preparation obtained from 12 recombinant clones were digested with Eco Rl and Mst II. One clone, pPT2KTPK, was found to contain the required insert of 900 bp. This DNA codes for a total of 300 amino acids, 182 amino acids for prothrombin (amino acids 67–248), a hexapeptide sequence and 112 amino acids for t-PA (amino acids 92–204).

The preparation of 385 bp DNA obtained by digestion of ptPBM-1 plasmid with Eco Rl and Asu lis described in FIG. 7. Two complementary oligonucleotide sequences of 12 bp each, were synthesized by the phosphotriester method. This linker restores the missing amino acids, Cys and Ala, of the prothrombin kringle region and is flanked by the Asu 1 and Mst II recognition sequences. About 500 ng of DNA (385 bp) was ligated with 1 μg of phosphorylated linker as shown in FIG. 13. After cutting with Eco Rl, a 402 bp DNA fragment was isolated. About equimolar amounts of 402 bp DNA and 900 bp DNA were ligated, cut with Eco Rl and a 1302 bp DNA fragment was isolated from the 1% agarose gel. This DNA was subcloned in Eco Rl cut pUC 13 vector. Plasmid DNA, isolated from 12 recombinant clones, was digested with Eco Rl. One clone, pNPT2KPAK, containing the required insert, was grown for large scale preparation of plasmid DNA. The plasmid DNA was digested to completion with Bam Hl and then partially with Nar 1 to obtain a 986 bp DNA fragment. Similarly, a 1300 bp DNA fragment was obtained from digestion of ptPBM-1 with Bam Hl and Nar 1. The two DNA fragments, 986 bp and 1300 bp, in equimolar amounts were ligated, cut with Bam Hl and a 2286 bp DNA fragment was isolated from 1% agarose gel electrophoresis. The DNA, flanked by the Bam Hl sequences, was inserted at the Bgl II site of the BPV expression vector. This DNA codes for a total of 752 amino acids-35 amino acids for the signal peptide and 717 amino acids for the mature protein. The mature protein, with an estimated molecular weight of about 92,000 contains 184 amino acids from the prothrombin double kringle region, a hexapeptide linker and complete t-PA sequence of 527 amino acids.

Expression and Biochemical Characterization of Hybrid Plasminogen Activators Two of the hybrid plasminogen activators (h-PA) shown in FIG. 1(a) and FIG. 1(b) were prepared for expression in the BPV-I based expression vector system. These h-PA's are throughout this application referred to as Hybrid A and Hybrid B, respectively.

Figure 5:
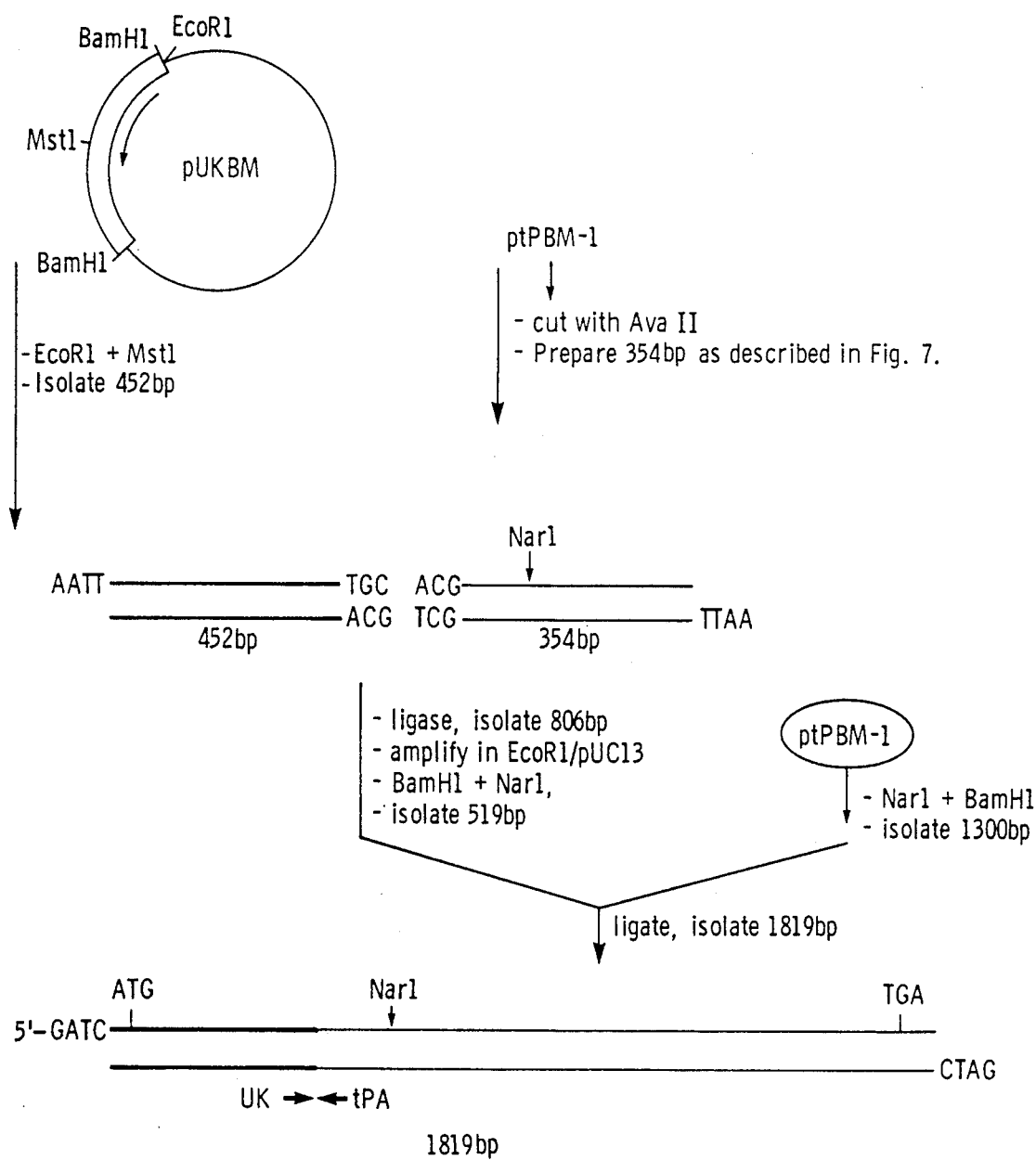
FIG. 5 presents a flow diagram of the method followed to produce the gene coding for the tris-kringle product depicted in FIG. 1(a).

The complete gene sequences, flanked by Bam HI for Hybrid A (1.8 Kb, FIG. 5) and Hybrid B (2.0 Kb, FIG. 7) were inserted into the Bgl II cut plasmid p341-3 (for details see Methods and Materials). Miniplasmid preparations from 12 recombinant clones were prepared and digested individually with Nar I, Bgl II or BamHI and Ava I. This was used to confirm the presence of hybrid genes as well as to determine the orientation of the insert. Only one orientation of the gene, i.e., in the direction of the metallothionein promotor, is desirable, because it places the expression of the gene under the control of that promotor. In addition, the SV40 poly-A sequence located just behind the gene, would process the RNA transcript of the gene by polyadenylation at its 3′-end for efficient translation of the gene. Two recombinant clones pHyb AMT-43 (for Hybrid A) and pHyb BMT-50 (for Hybrid B) were obtained.

Figure 14:
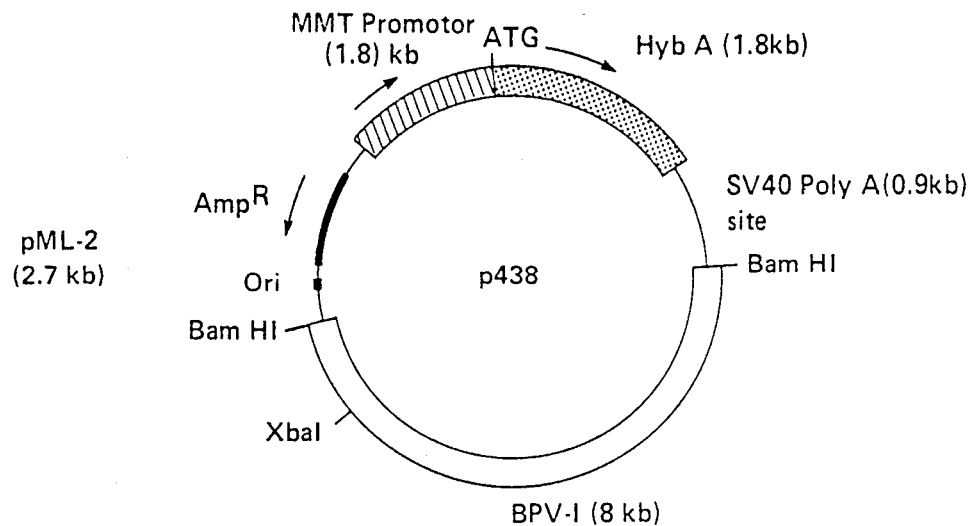
FIG. 14 presents a BPV-I based expression vector system designed for expression of plasminogen activator Hybrid A (corresponding to FIG. 1(a) and Hybrid B (corresponding to FIG. 1(b)) genes in mammalian cell line C-127 (mouse). The genes to be expressed, are inserted between the mouse metallothionein transcriptional promotor element and the SV40 early region transcriptional processing signals.
Figure 14:
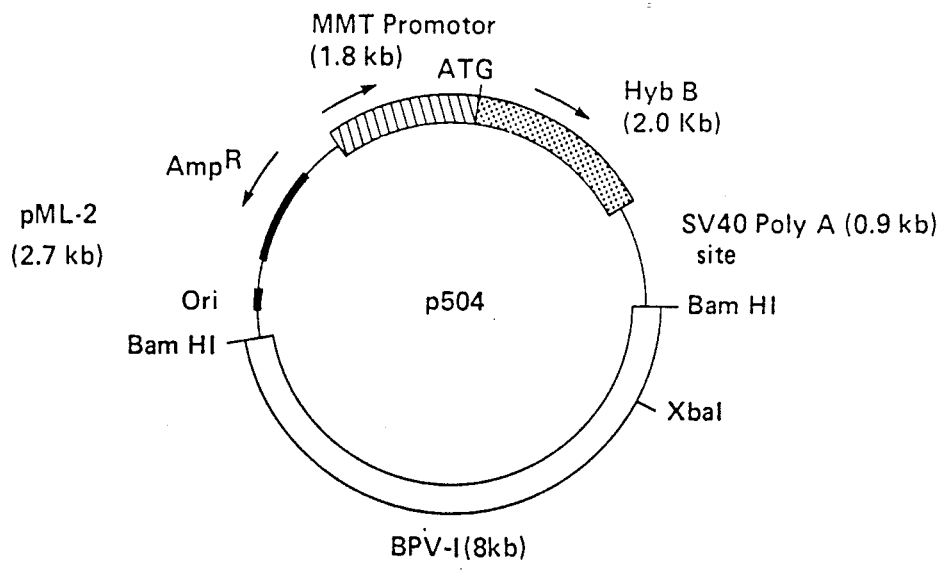

About 1 μg of the plasmid DNA obtained from the above mentioned clones, was digested with BamHI and then dephosphorylated with bacterial alkaline phosphatase. To this was inserted a complete 8.0 Kb BamHI cut BPV-I genome. Two expression plasmids pHyb-AMTBPV-438 and pHyb-BMTBPV-504 (simply referred to as p438 and p504) containing the genes coding for Hybrid A and Hybrid B, respectively, were obtained. A complete map showing the relative positions of various components of the expression plasmids is shown in FIG. 14.

The two expression plasmids containing the genes encoding for hybrid t-PA/urokinase molecules were transfected into mouse C127 cells by the calcium phosphate precipitation method (Graham et al., *Virology*, 52, 456 (1973)). Foci of morphologically transformed cells were subcultured and screened for gene expression. Initial screening for fibrinolytic activity in the medium was done on a fibrin-agar plate (Ploug et al. *Biochim. Biophys. Acta*, 24, 278 (1957)). From each transfection, an average of 50% of foci transformed with p504 (Hybrid B) and 5% of foci transformed with p438 (Hybrid A) showed positive fibrinolytic activity in the culture medium. Several high producers were selected and cell lines were expanded from individual foci. The two cell lines with which most of the preliminary biochemical and immunological characterizations of the gene products were performed were labeled clone 5A5 for Hybrid B and clone 16Cl for Hybrid A.

Biochemical Characterization

The enzymatic activities of the hybrid molecules were assessed by fibrinagar assay and amidolytic activity assay using synthetic substrates S-2444 and S-2251 (Shimoda et al., *Thromb. Haemostas.*, 46, 507 (1981)). Approximately 1–5 units/μl active enzyme were secreted into the medium in 16 to 18 hours. Natural t-PA and urokinase are synthesized as precursors and secreted from the cells after the signal sequences are cleaved off to become the mature protein. Furthermore, both t-PA and urokinase are glycosylated. To determine whether the h-PA's secreted by the transfected mouse cells were processed in a similar fashion as natural t-PA and urokinase, the hybrid molecules were analyzed by SDS/polyacrylamide gel (PAGE) electrophoresis followed by fibrin-agar overlay (Granelli-Piperno et al., *J. Exp. Med.*, 148, 223, (1978)). It was found that the active enzyme from Hybrid B-containing medium has a molecular weight of 76,000 and Hybrid A, 71,000. These are in good agreement with the molecular weight calculated from the inserted gene.

Hybrid B was purified from harvest medium in a manner similar to that used for t-PA purification. Amino acid sequence analysis indicated that the N-terminal of Hybrid B is correctly processed, having the sequence identical to the N-terminal region of mature t-PA: Ser-Tyr-Gln-; in addition, an N-terminal sequence, Ile-Lys-Gly-, corresponding to the amino acid at the activation cleavage site Arg-Ile was present. It is concluded that Hybrid B purified from the harvest medium existed mainly as an activated, two chain form. By addition of a protease inhibitor (Aprotinin) to the harvest medium, a single chain h-PA molecule is obtained.

Immunoprecipitation followed by SDS/PAGE of $^{35}$S-labeled harvest media showed that, under non-reducing conditions, bands at the position corresponding to an apparent molecular weight of 71,000–76,000 were observed in the sample from cell line 5A5 (Hybrid B) and 16Cl (Hybrid A), respectively, but not in the control sample. The fibrinolytic activity of the culture media from 5A5 cells as well as purified t-PA (American Diagnostics, Inc., Greenwich, CT) was neutralized by anti-t-PA antiserum, but not by anti-urokinase antiserum, suggesting that although the Hybrid B contains a urokinase kringle in addition to t-PA, the protease domain of Hybrid B was recognized and neutralized by anti-t-PA. Anti-urokinase antibody may bind to the urokinase kringle portion of the hybrid molecule, but this binding, if any, does not interfere with the proteolytic activity conferred by the protease domain at the C-terminus of the hybrid molecule.

The poly-kringle plasminogen activators of this invention are used in treatment of vascular accidents in mammals in the same manner and through the same delivery vehicles as t-PA itself. Thus the poly-kringle plasminogen activators of this invention may be formulated into pharmaceutical compositions by dissolving or suspending the polypeptides in suitable pharmaceutically acceptable vehicles known to the art as applied to t-PA. Administration to a mammal in need thereof by intravascular injection or infusion is conducted following techniques already established with t-PA itself. An intravenous primary dose of about 440 IU/kg body weight is normal, followed by continuing infusion of about 440 IU/kg/hr for about 6 to 12 hours is conventional practice when using t-PA.

What is claimed is:

1. A process for treating thrombosis in a mammal in need thereof which comprises administering into the vascular system of said mammal an effective amount of a human t-PA hybrid comprising at least both kringles of human t-PA and one or two heterologous kringles selected from the group consisting of the human urokinase kringle and either of the human prothrombin kringles.

2. A process of claim 1 in which said plasminogen activator is 91-(PTKaa$^{65-248}$-Ser-Glu-Gly-Asn-Ser-Asp)-92 t-PA.

3. The process of claim 1 in which said plasminogen activator is (UKaa$^{1-131}$-Ser-Glu-Gly-Asn-Ser-Asp)-$^{1-91}$ t-PA.

4. The process of claim 1 in which said plasminogen activator is 91-(UKaa$^{50-131}$-Ser-Glu-Gly-Asn-Ser-Asp)-92 t-PA.

5. The process of claim 1 in which said plasminogen activator is 261-(Ser-Glu-Gly-Asn-Ser-Asp-UKaa$^{50-131}$)-262 t-PA.

* * * * *